US011518776B2

(12) United States Patent
Sommazzi et al.

(10) Patent No.: US 11,518,776 B2
(45) Date of Patent: Dec. 6, 2022

(54) OXO-NITROGENATED IRON COMPLEX, CATALYTIC SYSTEM COMPRISING SAID OXO-NITROGENATED IRON COMPLEX AND PROCESS FOR THE (CO)POLYMERIZATION OF CONJUGATED DIENES

(71) Applicant: Versalis S.P.A., San Donato Milanese (IT)

(72) Inventors: Anna Sommazzi, Novara (IT); Guido Pampaloni, Pontedera (IT); Giovanni Ricci, Parma (IT); Francesco Masi, Santangelo Lodigiano (IT); Filippo Renili, Vicolungo (IT)

(73) Assignee: Versalis S.P.A., San Donato Milanese (IT)

( * ) Notice: Subject to any disclaimer, the term of this patent is extended or adjusted under 35 U.S.C. 154(b) by 275 days.

(21) Appl. No.: 16/345,015

(22) PCT Filed: Jan. 18, 2018

(86) PCT No.: PCT/IB2018/050308
§ 371 (c)(1),
(2) Date: Apr. 25, 2019

(87) PCT Pub. No.: WO2018/134757
PCT Pub. Date: Jul. 26, 2018

(65) Prior Publication Data
US 2021/0292354 A1  Sep. 23, 2021

(30) Foreign Application Priority Data

Jan. 20, 2017  (IT) ........................ 102017000006307

(51) Int. Cl.
*C08F 36/06* (2006.01)
*C08F 36/08* (2006.01)
*C07F 15/02* (2006.01)
*C07C 251/08* (2006.01)
*C08F 136/06* (2006.01)
*C08F 136/08* (2006.01)

(52) U.S. Cl.
CPC .......... *C07F 15/025* (2013.01); *C07C 251/08* (2013.01); *C08F 136/06* (2013.01); *C08F 136/08* (2013.01); *C07C 2601/16* (2017.05); *C08F 36/06* (2013.01)

(58) Field of Classification Search
CPC ...... C07F 15/025; C07F 15/02; C08F 4/7008; C08F 36/00; C08F 36/06; C08F 36/08
See application file for complete search history.

(56) References Cited

U.S. PATENT DOCUMENTS

| 3,151,047 | A | * | 9/1964 | Moon ................... B01D 3/146 203/82 |
| 3,373,177 | A | * | 3/1968 | Young .................. C07D 495/04 556/117 |
| 6,545,108 | B1 | * | 4/2003 | Moody ................. C07C 251/20 526/132 |
| 6,710,007 | B2 | * | 3/2004 | Brookhart ............. C07F 15/006 502/155 |
| 6,897,275 | B2 | | 5/2005 | Wang et al. |
| 7,060,768 | B2 | | 6/2006 | Brookhart et al. |
| 9,200,101 | B2 | * | 12/2015 | Ricci ........................ C08F 36/00 |
| 9,493,404 | B2 | * | 11/2016 | Sommazzi ............ C08F 136/06 |
| 10,066,044 | B2 | * | 9/2018 | Masi ..................... C08F 295/00 |
| 10,301,408 | B2 | * | 5/2019 | Pampaloni ............ C08F 4/6812 |
| 2003/0125485 | A1 | | 7/2003 | Brookhart et al. |
| 2004/0158012 | A1 | | 8/2004 | Brookhart et al. |
| 2015/0329577 | A1 | | 11/2015 | Sommazzi et al. |

FOREIGN PATENT DOCUMENTS

| CN | 1432027 A | 7/2003 |
| CN | 1626558 A | 6/2005 |

(Continued)

OTHER PUBLICATIONS

JP 2005-200305 A (Jul. 28, 2005) Katsuura, Akio et al.; machine translation. (Year: 2005).*

(Continued)

*Primary Examiner* — Rip A Lee
(74) *Attorney, Agent, or Firm* — Husch Blackwell LLP

(57) ABSTRACT

Oxo-nitrogenated iron complex having general formula (I): in which: $R_1$ and $R_2$, identical or different, represent a hydrogen atom; or they are selected from linear or branched, optionally halogenated $C_1$-$C_{20}$, preferably $C_1$-$C_{15}$, alkyl groups, optionally substituted cycloalkyl groups, optionally substituted aryl groups; $R_3$ represents a hydrogen atom, or it is selected from linear or branched, optionally halogenated $C_1$-$C_{20}$, preferably $C_1$-$C_{15}$ alkyl groups, optionally substituted cycloalkyl groups, optionally substituted aryl groups; X, identical or different, represent a halogen atom such as, for example, chlorine, bromine, iodine, preferably chlorine; or they are selected from. linear or branched $C_1$-$C_{20}$, preferably $C_1$-$C_{15}$, alkyl groups, —OCOR$_4$ groups or —OR$_4$ groups in which $R_4$ is selected from linear or branched $C_1$-$C_{20}$, preferably $C_1$-$C_{15}$, alkyl groups; n is 2 or 3. Said oxo-nitrogenated iron complex having general formula (I) can be advantageously used in a catalytic system for the (co)polymerization of conjugated dienes.

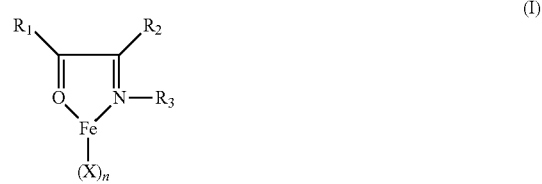

(I)

11 Claims, 22 Drawing Sheets

(56) References Cited

FOREIGN PATENT DOCUMENTS

| CN | 101186660 A | | 5/2008 | |
|---|---|---|---|---|
| CN | 104837876 A | | 8/2015 | |
| CN | 104837877 A | | 8/2015 | |
| JP | 2005-200305 | | 7/2005 | |
| JP | 2005-200305 A | * | 7/2005 | ........... C07D 233/58 |
| WO | 02/059165 A3 | | 8/2001 | |
| WO | 02/059165 A2 | | 8/2002 | |

OTHER PUBLICATIONS

Maurice S ; Brookhart et al, "Polymerization of olefinic compounds by polymerization catalyst complexes containing phosphino, amino, or imino groups", published Feb. 9, 2004.
International Search Report and Written Opinion for PCT/IB2018/050308 dated Mar. 15, 2018, 12 pages.
Vats, J.L. et al., Synthesis and Reactivity in Inorganic and Metal-Organic Chemistry, vol. 14, 1984, p. 69-82, Abstract.
Barbara Binotti et al., Journal of Organometallic Chemistry, 689, 2004, p. 647-661.
Hongren Chen et al., Chem. Asian J., 2014, 9, p. 3418-3430.
Henk van der Poel et al., Synthetic Communications, vol. 8, No. 5, Jan. 1, 1978, p. 305-313.

\* cited by examiner

OXO-NITROGENATED IRON COMPLEX, CATALYTIC SYSTEM COMPRISING SAID OXO-NITROGENATED IRON COMPLEX AND PROCESS FOR THE (CO)POLYMERIZATION OF CONJUGATED DIENES

FIELD OF THE INVENTION

The present invention relates to an oxo-nitrogenated iron complex.

More particularly, the present invention relates to an oxo-nitrogenated iron complex and its use in a catalytic system for the (co)polymerization of conjugated dienes.

The present invention also relates to a catalytic system for the (co)polymerization of conjugated dienes comprising said oxo-nitrogenated iron complex.

Furthermore, the present invention relates to a (co)polymerization process of conjugated dienes, in particular, a process for the polymerization of 1-3-butadiene or isoprene, characterized in that it uses said catalytic system.

Furthermore, the present invention also relates to a process for preparing the ligands having general formula (II) reported below, useful for the preparation of the aforementioned oxo-nitrogenated iron complex.

BACKGROUND

It is known that the stereospecific (co)polymerization of conjugated dienes is a very important process in the chemical industry in order to obtain products that are among the most widely used rubbers.

It is also known that among the different polymers that can be obtained from the stereospecific polymerization of 1,3-butadiene (i.e. 1,4-cis, 1,4-trans, 1,2 syndiotactic, 1,2 isotactic, 1,2 atactic, mixed structure 1,4-cis/1,2 having a variable 1,2 unit content), only 1,4-cis polybutadiene and 1,2 syndiotactic polybutadiene are industrially produced and commercialized. Further details on said polymers can be found, for example, in: Takeuchi Y. et al., "*New Industrial Polymers*", "*American Chemical Society Symposium Series*" (1974), Vol. 4, pag. 15-25; Halasa A. F. et al., "*Kirk-Othmer Encyclopedia of Chemical Technology*" (1989), 4th Ed., Kroschwitz J. I. Ed., John Wiley and Sons, New York, Vol. 8, pag. 1031-1045; Tate D. et al., "*Encyclopedia of Polymer Science and Engineering* (1989), 2nd Ed., Mark H. F. Ed., John Wiley and Sons, New York, Vol. 2, pag. 537-590; Kerns M. et al., "*Butadiene Polymers*", in "*Encyclopedia of Polymer Science and Technology*" (2003), Mark H. F. Ed., Wiley, Vol. 5, pag. 317-356.

Generally, 1,4-cis polybutadiene is prepared through polymerization processes that use different catalytic systems comprising catalysts based on titanium (Ti), cobalt (Co), nickel (Ni), neodymium (Nd). Catalytic systems comprising cobalt based catalysts have high catalytic activity and stereospecificity and can be considered the most versatile of those mentioned above since, when their formulation is changed, they are able to provide all the possible stereoisomers of polybutadiene mentioned above, as described, for example, in: Porri L. et al., "*Comprehensive Polymer Science*" (1989), Eastmond G. C. et al. Eds., Pergamon Press, Oxford, UK, Vol. 4, Part II, pag. 53-108; Thiele S. K. H. et al., "*Macromolecular Science. Part C: Polymer Reviews*" (2003), C43, pag. 581-628; Osakada, K. et al., "*Advanced Polymer Science*" (2004), Vol. 171, pag. 137-194; Friebe L. et al., "*Advanced Polymer Science*" (2006), Vol. 204, pag. 1-154.

Iron (Fe) based catalysts have also been studied which are useful in the (co)polymerization of conjugated dienes. One of the first studies in literature on catalytic systems comprising iron (Fe) based catalysts concerned the polymerization of 1,3-butadiene with catalytic systems comprising iron acetylacetonate [Fe(acac)$_3$], tri-iso-butyl-aluminum (TIBA) and 1,10-phenanthroline (phen) as described, for example, in Zhang Z. Y. et al., "*Journal of Molecular Catalysis*" (1982), Vol. 17, Issue 1, pag. 65-76. Said catalytic system is able to provide a binary polybutadiene with a mixed 1,4-cis/1,2 structure having an equal content of 1,4-cis and 1,2 units.

U.S. Pat. No. 6,160,063 describes a catalytic system obtained by combination or reaction of: a compound containing iron (for example, iron carboxylate, iron β-diketonate, iron alkoxide, iron arylalkoxide); an organic compound of magnesium; and a cyclic hydrogen phosphite. The aforementioned catalytic system is particularly useful for the polymerization of 1,3-butadiene for providing binary polybutadiene with a mixed 1,4-cis/1,2 structure.

U.S. Pat. No. 6,180,734 describes a catalytic system obtained by combination or reaction of: a compound containing iron (for example, iron carboxylate, iron β-diketonate, iron alkoxide, iron arylalkoxide); a cyclic hydrogen phosphite; and an organic compound of aluminum. The aforementioned catalytic system is particularly useful for the polymerization of 1,3-butadiene for providing 1,2 syndiotactic polybutadiene.

U.S. Pat. No. 6,211,313 describes a catalytic system obtained by combination or reaction of: a compound containing iron (for example, iron carboxylate, iron β-diketonate, iron alkoxide, iron arylalkoxide); a cyclic hydrogen phosphite; and an aluminoxane. The aforementioned catalytic system is particularly useful for the polymerization of 1,3-butadiene for providing 1,2 syndiotactic polybutadiene.

U.S. Pat. No. 6,277,779 describes a catalytic system obtained by combination or reaction of: a compound containing iron (for example, iron carboxylate, iron β-diketonate, iron alkoxide, iron arylalkoxide); a dihydrocarbyl hydrogen phosphite; and an organic compound of aluminum. The aforementioned catalytic system is particularly useful for the polymerization of 1,3-butadiene for providing 1,2 syndiotactic polybutadiene having a melting point that can vary from 100° C. to 200° C., according to the components and the ratios between the different components present in said catalytic system.

U.S. Pat. Nos. 6,284,702 and 6,388,030 describe a catalytic system obtained by combination or reaction of: a compound containing iron (for example, iron carboxylate, iron β-diketonate, iron alkoxide, iron arylalkoxide); an organic compound of magnesium; and a dihydrocarbyl hydrogen phosphite. The aforementioned catalytic system is particularly useful for the polymerization of 1,3-butadiene for providing 1,2 syndiotactic polybutadiene having a melting point that can vary from 100° C. to 190° C., according to the components and the ratios between the different components present in said catalytic system.

Catalytic systems comprising, for example, iron diethyl bis(2,2'-bipyridine) [FeEt$_2$(bipy)$_2$] and methylaluminoxane (MAO), or comprising various iron dichloride (FeCl$_2$) complexes with bidentate amines (for example, N,N,N',N'-tetramethylethylenediamine (tmeda), N,N'-dimethylethylenediamine (dmeda), 2,2'-bipyridine (bipy), 1,10-phenanthroline (phen), and compounds of aluminum [for example, aluminum alkyls (AlR$_3$ in which R is ethyl, iso-butyl), methylaluminoxane (MAO)], are extremely active in the (co)polymerization of conjugated dienes, as described, for example, in international patent application WO 02/102861; or in Bazzini C. et al., "*Macromolecular Rapid Communications*" (2002), Vol. 23(15), pag. 922-927; Bazzini C. et al., "*Polymer Communication*" (2004), Vol. 45, pag. 2871-2875; Ricci G. et al., "*Journal of Molecular Catalysis A: Chemical*" (2003), Vol. 204-205, pag. 287-293; Ricci G. et al., "*Coordination Chemistry Reviews*" (2010), Vol. 254, Issues 5-6, pag. 661-676. Such catalytic systems are able to provide polybutadienes with a prevalently 1,2 structure; in particular, the polybutadienes obtained at low temperatures have an approximately 90% 1,2 structure and a 50% syndiotactic pentade structure, and the 1,2 unit and syndiotactic pentade contents are reduced as the polymerization temperature increases. Furthermore, the polybutadienes obtained with the aforementioned catalytic systems have a very high weight-average molecular weight ($M_w$) and a rather restricted polydispersion index—PDI—corresponding to the ratio $M_w/M_n$ ($M_n$=number-average molecular weight) e.g., ranging from 1 to 2, indicating a "pseudo-living" nature of said catalytic systems which are indicated as "single site". A significant effect of the nature of the amine ligand on the catalytic activity of said catalytic systems has also been observed: in particular, the catalytic activity is reduced as the steric encumbrance of the ligand increases. Furthermore, the type of aluminum compound may also affect the catalytic activity: in fact, it has been observed that when methylaluminoxane (MAO) is used, there is an increase in the 1,2 unit content under the same polymerization conditions. Furthermore, the aforementioned catalytic systems were shown to be extremely active and selective not only in the polymerization of 1,3-butadiene but also in the (co)polymerization of other conjugated dienes, such as, for example, isoprene, 2,3-dimethyl-1,3-butadiene, 3-methyl-1,3-pentadiene, providing (co)polymers with different structures, such as, for example, 3,4 syndiotactic polyisoprene, poly(2,3-dimethyl-1,3-butadiene) 1,4-cis, poly(3-methyl-1,3-pentadiene) E-1,2-syndiotactic.

Catalytic systems comprising iron terpyridine complexes [for example, $FeCl_3$(terpyridine)], in combination with appropriate alkylating agents, are useful in the stereospecific polymerization of conjugated dienes: said catalytic systems show discrete catalytic activity and are able to provide polybutadienes with a 1,4-trans structure as described, for example, in Nakayama Y. et al., "*Macromolecules*" (2003), Vol. 36(21), pag. 7953-7958.

Catalytic systems obtained through the combination of iron (III) carboxylates (for example, iron (III) 2-ethylhexanoate [Fe(2-EHA)$_3$] with aluminum tri-iso-butyl (Al$^i$Bu$_3$) in hexane, in the presence of phosphates (for example, triethylphosphate) are able to polymerize 1,3-butadiene to polybutadiene with a prevalently 1,2 structure and with a high degree of syndiotacticity as described, for example, in Gong D. et al., "*Polymer*" (2009), Vol. 50, pag. 5980-5986.

Catalytic systems comprising complexes obtained from iron (III) chloride (FeCl$_3$) or from iron(II) chloride tetrahydrate (FeCl$_2$.4H$_2$O) with substituted 2,6-bis[1-(iminophenyl)ethyl]pyridine or 2,6-bis(imino)pyridine, in the presence of methylaluminoxane (MAO), are able to provide high 1,4-trans structure (>90%) or 1,4-cis/1,4-trans mixed structure polybutadienes, as a function of the catalytic system used as described, for example, in Gong D. et al., "*Polymer*" (2009), Vol. 50, pag. 6259-6264; Gong D. et al., "*Inorganica Chimica Acta*" (2011), Vol. 373, Issue 1, pag. 47-53. Catalytic systems comprising complexes obtained from iron (III) chloride (FeCl$_3$) or from iron(II) chloride tetrahydrate (FeCl$_2$.4H$_2$) with substituted 2,6-bis[1-(2-benzimidazolyl)] pyridine or 2,6-bis(pyrazol)pyridine, in the presence of modified methylaluminoxane (MMAO) or diethylaluminum chloride (AlEt$_2$Cl), are able to provide polybutadienes with a different structure, i.e. 1,4-trans or 1,4-cis, as a function of the catalytic system used as described, for example, in Gong D. et al., "*Journal of Organometallic Chemistry*" (2012), Vol. 702, pag. 10-18.

Pincer bis-imine complexes of iron (II) [Fe(II) in combination with aluminum alkyl [for example, tri-methylaluminum (AlMe$_3$)] are able to provide polybutadienes with an essentially 1,4-cis structure (≥70%) as described, for example, in Zhang J. et al., "*Dalton Transactions*" (2012), Vol. 41, pag. 9639-9645.

Catalytic systems comprising imine-pyridine complexes of iron (II), aluminum alkyls (for example, AlR$_3$ in which R is ethyl, iso-butyl), and boron salts, are able to polymerize isoprene to polyisoprene with a high 1,4-trans structure as described, for example, in Raynaud J. et al., "*Angewandte Chemie International Edition*" (2012), Vol. 51, pag. 11805-11808; or in international patent application WO 2012/109343.

Catalytic systems comprising iron (II) complexes with substituted 2-pyrazole-1,10-phenanthroline and aluminum alkyls (for example, AlR$_3$ in which R is ethyl, iso-butyl, octyl), are characterized by high catalytic activity and selectivity and are able to provide polybutadienes with a high 1,4-trans structure as described, for example, in Wang B. et al., "*Polymer*" (2013), Vol. 54, pag. 5174-5181.

Catalytic systems comprising iron (II) complexes with 2-(N-arylcarboxyimidoylchloride)quinoline and aluminum alkyls [for example, AlR$_3$ in which R is ethyl, iso-butyl; or methylaluminoxane (MAO)], are characterized by low catalytic activity and are able to provide polybutadienes with a high 1,4-cis structure as described, for example, in Liu H. et al., "*Journal of Molecular Catalysis A: Chemical*" (2014), Vol. 391, pag. 25-35.

Catalytic systems comprising iron (II) complexes with 2,6-bis(dimethyl-2-oxazoline-2-yl)pyridine and aluminum alkyls [for example, AlR$_3$ in which R is ethyl, iso-butyl; or methylaluminoxane (MAO)], are able to provide polybutadienes with a mixed 1,4-cis/1,4-trans structure as described, for example, in Gong D. et al., "*Journal of Molecular Catalysis A: Chemical*" (2015), Vol. 406, pag. 78-84.

Finally, polybutadienes with "soft/hard" stereoblocks, with a mixed 1,4-cis/1,2 structure were obtained using the catalytic system 2-ethylhexanoate of iron/tri-iso-butylaluminum/diethyl phosphate [Fe(2-EHA)$_3$/Al$^i$Bu)$_3$/DEP], by appropriately varying the aluminum/iron (Al/Fe) ratio as described, for example, in Zheng W. et al., "*Journal of Polymer Science Part A: Polymer Chemistry*" (2015), Vol. 53, Issue 10, pag. 1182-1188.

DETAILED DESCRIPTION

Figure 1:
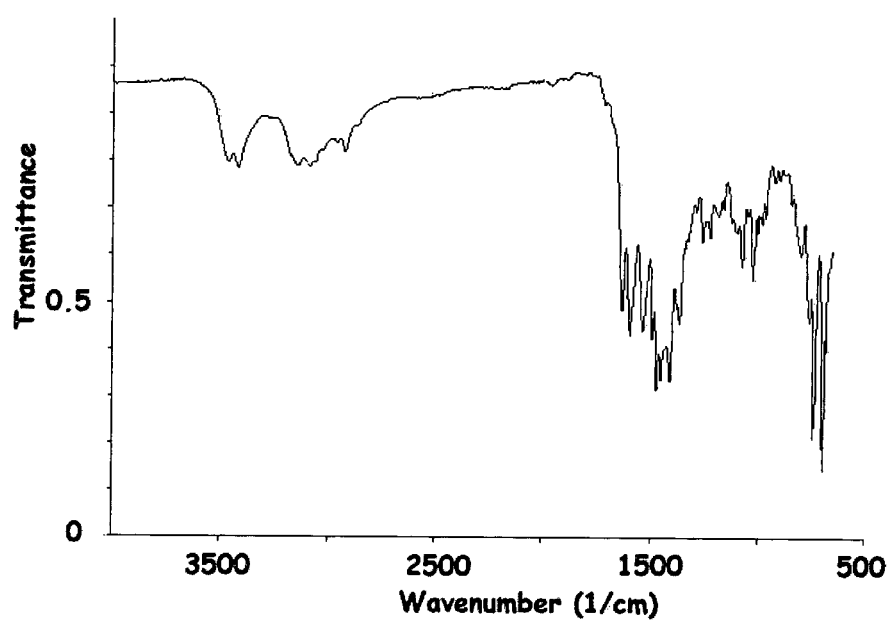
FIG. 1 is the FT-IR spectrum of Example 7.

Since (co)polymers of conjugated dienes, in particular polybutadiene and polyisoprene, can be advantageously used in various sectors such as, for example, in the automotive sector for producing tires, in particular for tire treads, as well as in the footwear industry (for example, for producing soles for shoes), the study of new catalytic systems able to provide said (co)polymers is still of great interest.

The Applicant has faced the problem of finding a new oxo-nitrogenated iron complex to be used in a catalytic system able to provide (co)polymers of conjugated dienes such as, for example, linear or branched polybutadiene or linear or branched polyisoprene, with a mixed structure, in particular, polybutadiene with a prevalent 1,4-cis and 1,2 unit content (i.e. having a content of 1,4-cis and 1,2 units≥90%, preferably equal to 100%), and polyisoprene with a prevalent content of 1,4-cis and 3,4 units (i.e. having a content of 1,4-cis and 3,4 units≥90%, preferably equal to 100%).

The Applicant has now found a new oxo-nitrogenated iron complex having general formula (I) defined below, that can be used in a catalytic system able to provide (co)polymers of conjugated dienes such as, for example, linear or branched polybutadiene or linear or branched polyisoprene, with a mixed structure, in particular, polybutadiene with a prevalent 1,4-cis and 1,2 unit content (i.e. having a content of 1,4-cis and 1,2 units≥90%, preferably equal to 100%), and polyisoprene with a prevalent content of 1,4-cis and 3,4 units (i.e. having a content of 1,4-cis and 3,4 units≥90%, preferably equal to 100%). In fact, said catalytic system allows the microstructure of conjugated diene (co)polymers to be modulated, i.e. the 1,4-cis, 1,4-trans and 1,2 unit content in the polybutadiene and the 1,4-cis, 1,4-trans and 3,4 unit content in the polyisoprene, according to the different final uses (e.g., use for manufacturing tires or for producing soles for shoes).

Therefore, the subject matter of the present invention is an oxo-nitrogenated iron complex having general formula (I):

in which:

R$_1$ and R$_2$, identical or different, represent a hydrogen atom; or they are selected from linear or branched, optionally halogenated C$_1$-C$_{20}$, preferably C$_1$-C$_{15}$, alkyl groups, optionally substituted cycloalkyl groups, optionally substituted aryl groups;

R$_3$ represents a hydrogen atom, or it is selected from linear or branched, optionally halogenated C$_1$-C$_{20}$, preferably C$_1$-C$_{15}$, alkyl groups, optionally substituted cycloalkyl groups, optionally substituted aryl groups;

X, identical or different, represent a halogen atom such as, for example, chlorine, bromine, iodine, preferably chlorine; or they are selected from linear or branched C$_1$-C$_{20}$, preferably C$_1$-C$_{15}$, alkyl groups, —OCOR$_4$ groups or —OR$_4$ groups in which R$_4$ is selected from linear or branched C$_1$-C$_{20}$, preferably C$_1$-C$_{15}$, alkyl groups;

n is 2 or 3.

For the purpose of the present description and of the following claims, the definitions of the numeric ranges always include the extremes unless specified otherwise.

For the purpose of the present description and of the following claims, the term "comprising" also includes the terms "which essentially consists of" or "which consists of".

For the purpose of the present description and of the following claims, the term "C$_1$-C$_{20}$ alkyl groups" means alkyl groups having from 1 to 20 carbon atoms, linear or branched. Specific examples of C$_1$-C$_{20}$ alkyl groups are: methyl, ethyl, n-propyl, iso-propyl, n-butyl, s-butyl, iso-butyl, tert-butyl, pentyl, hexyl, heptyl, octyl, n-nonyl, n-decyl, 2-butyloctyl, 5-methylhexyl, 4-ethylhexyl, 2-ethylheptyl, 2-ethylhexyl.

For the purpose of the present description and of the following claims, the term "optionally halogenated C$_1$-C$_{20}$ alkyl groups" means alkyl groups having from 1 to 20 carbon atoms, linear or branched, saturated or unsaturated, in which at least one of the hydrogen atoms is substituted with a halogen atom such as, for example, fluorine, chlorine, bromine, preferably fluorine, chlorine. Specific examples of C$_1$-C$_{20}$ alkyl groups optionally halogenated are: fluoromethyl, difluoromethyl, trifluoromethyl, trichloromethyl, 2,2,2-trifluoroethyl, 2,2,2-trichloroethyl, 2,2,3,3-tetrafluoropropyl, 2,2,3,3,3-pentafluoropropyl, perfluoropentyl, perfluoroctyl, perfluorodecyl.

For the purpose of the present description and of the following claims, the term "cycloalkyl groups" means cycloalkyl groups having from 3 to 30 carbon atoms. Said cycloalkyl groups can be optionally substituted with one or more groups, identical or different, selected from: halogen atoms; hydroxyl groups, C$_1$-C$_{12}$ alkyl groups; C$_1$-C$_{12}$ alkoxy groups; cyano groups; amino groups; nitro groups. Specific examples of cycloalkyl groups are: cyclopropyl, 2,2-difluorocyclopropyl, cyclobutyl, cyclopentyl, cyclohexyl, hexamethylcyclohexyl, pentamethlylcyclopentyl, 2-cyclooctylethyl, methylcyclohexyl, methoxycyclohexyl, fluorocyclohexyl, phenylcyclohexyl.

For the purpose of the present description and of the following claims, the term "aryl groups" means carbocyclic aromatic groups. Said aryl groups can be optionally substituted with one or more groups, identical or different, selected from: halogen atoms such as, for example, fluorine, chlorine, bromine; hydroxyl groups, $C_1$-$C_{12}$ alkyl groups; $C_1$-$C_{12}$ hydroxyl groups; cyano groups; amino groups; nitro groups. Specific examples of aryl groups are: phenyl, methylphenyl, trimethylphenyl, methoxyphenyl, hydroxyphenyl, phenyloxyphenyl, fluorophenyl, pentafluorophenyl, chlorophenyl, bromophenyl, nitrophenyl, dimethylaminophenyl, naphthyl, phenylnaphthyl, phenanthrene, anthracene.

In accordance with a preferred embodiment of the present invention, in said oxo-nitrogenated iron complex having general formula (I):
- $R_1$ and $R_2$, mutually identical, are selected from linear or branched $C_1$-$C_{20}$ alkyl groups, preferably are a methyl group;
- $R_3$ is selected from phenyl groups optionally substituted with linear or branched $C_1$-$C_{20}$ alkyl groups, preferably substituted with one or more methyl, ethyl, iso-propyl, tert-butyl groups;
- X, identical, are a halogen atom such as, for example, chlorine, bromine, iodine, preferably chlorine;
- n is 2 or 3.

The oxo-nitrogenated iron complex having general formula (I) can be considered, in accordance with the present invention, under any physical form such as, for example, the isolated and purified solid form, the form solvated with an appropriate solvent, or the one supported on suitable organic or inorganic solids, preferably having a granular or powdered physical form.

The oxo-nitrogenated iron complex having general formula (I) is prepared starting from ligands having general formula (II):

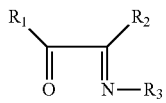
(II)

in which:
- $R_1$ and $R_2$, identical or different, represent a hydrogen atom; or they are selected from linear or branched, optionally halogenated $C_1$-$C_{20}$, preferably $C_1$-$C_{15}$, alkyl groups, optionally substituted cycloalkyl groups, optionally substituted aryl groups;
- $R_3$ represents a hydrogen atom, or it is selected from linear or branched, optionally halogenated $C_1$-$C_{20}$, preferably $C_1$-$C_{15}$, alkyl groups, optionally substituted cycloalkyl groups, optionally substituted aryl groups.

As mentioned above, the present invention also relates to a process for preparing ligands having general formula (II).

Therefore, the present invention relates to a process for preparing a ligand having general formula (II):

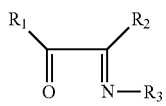
(II)

in which $R_1$, $R_2$ and $R_3$, have the same meanings described above, comprising reacting at least one primary amine having general formula (III):

$$H_2N-R_3 \qquad (III)$$

in which $R_3$ has the same meanings described above, with at least one compound having general formula (IV):

(IV)

in which $R_1$ and $R_2$, have the same meanings described above;
in the presence of water, at a temperature ranging from 18° C. to 30° C., preferably at room temperature, for a time ranging from 1 hour to 10 days, preferably ranging from 1.5 hours to 8 days.

In accordance with a preferred embodiment of the present invention, said primary amine having general formula (III) and said compound having general formula (IV) can be used in a molar ratio ranging from 1:10 to 1:2, preferably ranging from 1:5 to 1:1.5.

For the purpose of obtaining the ligand having general formula (II) with high purity, said process may comprise a fractional distillation step.

In accordance with a preferred embodiment of the present invention, said process may comprise a fractional distillation step.

Preferably, the water used in the aforementioned process is distilled water.

Specific examples of primary amines having general formula (III) useful for the purpose of the aforementioned process are: aniline, o-toluidine, m-toluidine, p-toluidine, 2-iso-propylaniline, 2-tert-butylaniline, 2-ethylaniline, 2,6-dimethylaniline, 2,6-diethylaniline, 2,4,6-trimethylaniline, benzylamine, cyclohexylamine, or mixtures thereof.

Specific examples of compounds having general formula (IV) are: 2,3-butanedione, 1-phenyl-1,3-butanedione, methylglyoxal, 2,3-pentanedione, 2,3-hexanedione, or mixtures thereof.

Specific examples of ligands having general formula (II) useful for the purpose of the present invention are those having the following formulae (L1)-(L6):

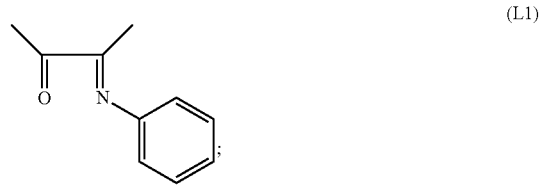
(L1)

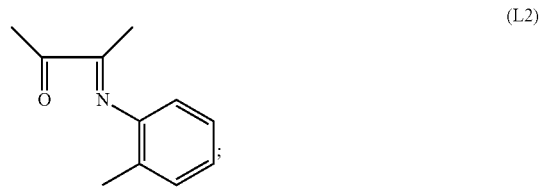
(L2)

-continued

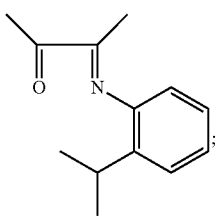
(L3)

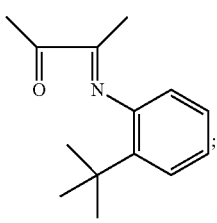
(L4)

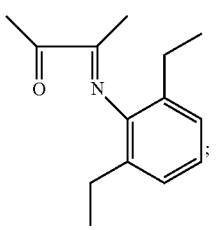
(L5)

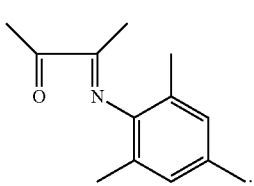
(L6)

The oxo-nitrogenated iron complex having general formula (I) may be prepared according to processes known in the prior art. For example, said oxo-nitrogenated iron complex may be prepared by reaction between iron compounds having general formula $Fe(X)_2$ or $Fe(X)_3$ in which X is a halogen atom such as, for example, chlorine, bromine, iodine, preferably chlorine, as such or complexed with ethers [for example, diethylether, tetrahydrofuran (THF), 1,2-dimethoxyethane], or with water, with the ligands having formulae (L1)-(L6) reported above, in molar ratio ligand (L)/iron (Fe) ranging from 1 to 2, operating, preferably, in the presence of at least one solvent which can be selected, for example, from: chlorinated solvents (for example, dichloromethane), ether solvents, [for example, tetrahydrofuran (THF), 1,2 dimethoxyethane], alcoholic solvents (for example, butanol), hydrocarbon solvents (for example, hexane), or mixtures thereof, at room temperature or higher. The oxo-nitrogenated iron complex thus obtained may be subsequently recovered through known methods such as, for example, evaporation of the solvent (for example, under vacuum), followed by washing with solvent (for example, heptane) and by drying (for example, under vacuum). More details on the process for the preparation of said oxo-nitrogenated iron complex having general formula (I) can be found in the following examples.

For the purpose of the present description and of the following claims the wording "room temperature" means a temperature ranging from 20° C. to 25° C.

As mentioned above, the present invention also relates to a catalytic system for the (co)polymerization of conjugated dienes comprising said oxo-nitrogenated iron complex having general formula (I).

Therefore, the present invention also relates to a catalytic system for the (co)polymerization of conjugated dienes comprising:
(a) at least one oxo-nitrogenated iron complex having general formula (I);
(b) at least one co-catalyst selected from organic compounds of an element M' different from carbon, said element M' being selected from elements belonging to groups 2, 12, 13, or 14, of the Periodic Table of the Elements, preferably from: boron, aluminum, zinc, magnesium, gallium, tin, more preferably from aluminum, boron.

In general, the formation of the catalytic system comprising the oxo-nitrogenated iron complex having general formula (I) and the co-catalyst (b), is preferably carried out in an inert liquid medium, more preferably in a hydrocarbon solvent. The choice of the oxo-nitrogenated iron complex having general formula (I) and of the co-catalyst (b), as well as the particular methodology used, may vary according to the molecular structures and the desired result, according to what is similarly reported in relevant literature accessible to an expert skilled in the art for other transition metal complexes with imine ligands, as reported, for example, by L. K. Johnson et al., in "Journal of the American Chemical Society" (1995), Vol. 117, pag. 6414-6415, and by van Koten G. et al., in "Advances in Organometallic Chemistry" (1982), Vol. 21, pag. 151-239.

In accordance with a further preferred embodiment of the present invention, said co-catalyst (b) can be selected from ($b_1$) aluminum alkyls having general formula (V):

$$Al(X')_n(R_5)_{3-n} \qquad (V)$$

in which X' represents a halogen atom such as, for example, chlorine, bromine, iodine, fluorine; $R_5$, identical or different, represent a hydrogen atom, or they are selected from linear or branched $C_1$-$C_{20}$ alkyl groups, cycloalkyl groups, aryl groups, said groups being optionally substituted with one or more silicon or germanium atoms; and n is an integer ranging from 0 to 2.

In accordance with a further preferred embodiment of the present invention, said co-catalyst (b) can be selected from ($b_2$) organo-oxygenated compounds of an element M' different from carbon belonging to groups 13 or 14 of the Periodic Table of the Elements, preferably organo-oxygenated compounds of aluminum, gallium, tin. Said organo-oxygenated compounds ($b_2$) can be defined as organic compounds of M', in which the latter is bonded to at least one oxygen atom and at least one organic group consisting of an alkyl group having from 1 to 6 carbon atoms, preferably methyl.

In accordance with a further preferred embodiment of the present invention, said co-catalyst (b) can be selected from ($b_3$) compounds or mixtures of organometallic compounds of an element M' different from carbon able to react with the oxo-nitrogenated iron complex having general formula (I) by extracting from it a σ-linked substituent $X_1$ or $X_2$, to form on the one hand at least one neutral compound and, on the other hand, an ionic compound consisting of a cation containing the metal (Fe) coordinated by the ligand, and of a non-coordinating organic anion containing the metal M', whose negative charge is delocalized on a multicentric structure.

It is to be noted that for the purpose of the present invention and of the following claims, the term "Periodic Table of the Elements" refers to the "IUPAC Periodic Table of the Elements", version dated 22 Jun. 2007, available on the following website: www.iupac.orq/fileadmin/user_upload/news/IUPAC_Periodic_Table-1Jun12.pdf.

Specific examples of aluminum alkyls having general formula (V) particularly useful for the purpose of the present invention are: tri-methyl-aluminum, tri-(2,3,3-tri-methyl-butyl)-aluminum, tri-(2,3-di-methyl-hexyl)-aluminum, tri-(2,3-di-methyl-butyl)-aluminum, tri-(2,3-di-methyl-pentyl)-aluminum, tri-(2,3-di-methyl-heptyl)-aluminum, tri-(2-methyl-3-ethyl-pentyl)-aluminum, tri-(2-methyl-3-ethyl-hexyl)-aluminum, tri-(2-methyl-3-ethyl-heptyl)-aluminum, tri-(2-methyl-3-propyl-hexyl)-aluminum, tri-ethyl-aluminum, tri-(2-methyl-3-methyl-butyl)-aluminum, tri-(2-ethyl-3-methyl-pentyl)-aluminum, tri-(2,3-di-ethyl-pentyl-aluminum), tri-n-propyl-aluminum, tri-iso-propyl-aluminum, tri-(2-propyl-3-methyl-butyl)-aluminum, tri-(2-iso-propyl-3-methyl-butyl)-aluminum, tri-n-butyl-aluminum, tri-iso-butyl-aluminum (TIBA), tri-tert-butyl-aluminum, tri-(2-iso-butyl-3-methyl-pentyl)-aluminum, tri-(2,3,3-tri-methyl-pentyl)-aluminum, tri-(2,3,3-tri-methyl-hexyl)-aluminum, tri-(2-ethyl-3,3-di-methyl-butyl)-aluminum, tri-(2-ethyl-3,3-di-methyl-pentyl)-aluminum, tri-(2-iso-propyl-3,3-di-methyl-butyl)-aluminum, tri-(2-tri-methylsilyl-propyl)-aluminum, tri-2-methyl-3-phenyl-butyl)-aluminum, tri-(2-ethyl-3-phenyl-butyl)-aluminum, tri-(2,3-di-methyl-3-phenyl-butyl)-aluminum, tri-(2-phenyl-propyl)-aluminum, tri-[2-(4-fluoro-phenyl)-propyl]-aluminum, tri-[2-(4-chloro-phenyl)-propyl]-aluminum, tri-[2-(3-iso-propyl-phenyl-tri-(2-phenyl-butyl)-aluminum, tri-(3-methyl-2-phenyl-butyl)-aluminum, tri-(2-phenyl-pentyl)-aluminum, tri-[2-(penta-fluoro-phenyl)-propyl]-aluminum, tri-(2,2-diphenyl-ethyl]-aluminum, tri-(2-phenyl-methyl-propyl]-aluminum, tri-pentyl-aluminum, tri-hexyl-aluminum, tri-cyclohexyl-aluminum, tri-octyl-aluminum, di-ethyl-aluminum hydride, di-n-propyl-aluminum hydride, di-n-butyl-aluminum hydride, di-iso-butyl-aluminum hydride (DIBAH), di-hexyl-aluminum hydride, di-iso-hexyl-aluminum hydride, di-octyl-aluminum hydride, di-iso-octyl-aluminum hydride, ethyl-aluminum di-hydride, n-propyl-aluminum di-hydride, iso-butyl-aluminum di-hydride, di-ethyl-aluminum chloride (DEAC), mono-ethyl-aluminum dichloride (EADC), di-methyl-aluminum chloride, di-iso-butyl-aluminum chloride, iso-butyl-aluminum dichloride, ethyl-aluminum-sesquichloride (EASC), as well as the corresponding compounds in which one of the hydrocarbon substituents is substituted by a hydrogen atom and those in which one or two of the hydrocarbon substituents are substituted with an iso-butyl group. Di-iso-butyl-aluminum hydride (DIBAH) di-ethyl-aluminum chloride (DEAC), mono-ethyl-aluminum dichloride (EADC), ethylaluminum-sesquichloride (EASC), are particularly preferred.

Preferably, when used for the formation of a catalytic (co)polymerization system in accordance with the present invention, the aluminum alkyls having general formula (V) can be placed in contact with an oxo-nitrogenated iron complex having general formula (I), in proportions such that the molar ratio between the iron contained in the oxo-nitrogenated iron complex having general formula (I) and the aluminum contained in the aluminum alkyls having general formula (V) can be ranging from 5 to 5000, preferably ranging from 10 to 1000. The sequence with which the oxo-nitrogenated iron complex having general formula (I) and the aluminum alkyl having general formula (II) are placed in contact with each other is not particularly critical.

Further details on aluminum alkyls having general formula (V) can be found in international patent application WO 2011/061151.

In accordance with a particularly preferred embodiment, said organo-oxygenated compounds ($b_2$) can be selected from the aluminoxanes having general formula (VI):

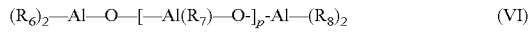

$(R_6)_2\text{—Al—O—}[\text{—Al}(R_7)\text{—O—}]_p\text{-Al—}(R_8)_2$ (VI)

in which $R_6$, $R_7$ and $R_8$, identical or different, represent a hydrogen atom, or a halogen atom such as, for example, chlorine, bromine, iodine, fluorine; or they are selected from linear or branched $C_1$-$C_{20}$ alkyl groups, cycloalkyl groups, aryl groups, said groups being optionally substituted with one or more silicon or germanium atoms; and p is an integer ranging from 0 to 1000.

As it is known, aluminoxanes are compounds containing Al—O—Al bonds, with a variable O/Al ratio, obtainable according to processes known in the prior art such as, for example, by reaction, in controlled conditions, of an aluminum alkyl or an aluminum alkyl halogenide, with water, or with other compounds containing predetermined quantities of available water such as, for example, in the case of the reaction of aluminum trimethyl with aluminum sulfate hexahydrate, copper sulfate pentahydrate, or iron sulfate pentahydrate.

Said aluminoxanes and, in particular, methylaluminoxane (MAO), are compounds that can be obtained through known organometallic chemical processes such as, for example, by adding trimethyl aluminum to a suspension in aluminum sulfate hexahydrate.

Preferably, when used for the formation of a catalytic (co)polymerization system in accordance with the present invention, the aluminoxanes having general formula (VI) can be placed in contact with an oxo-nitrogenated iron complex having general formula (I), in proportions such that the molar ratio between the aluminum (Al) contained in the aluminoxane having general formula (VI) and the iron contained in the oxo-nitrogenated iron complex having general formula (I) is ranging from 10 to 10000, preferably ranging from 100 to 5000. The sequence with which the oxo-nitrogenated iron complex having general formula (I) and the aluminoxane having general formula (VI) are placed in contact with each other is not particularly critical.

As well as the aforementioned preferred aluminoxanes having general formula (VI), the definition of the compound ($b_2$) in accordance with the present invention also includes galloxanes in which, in the general formula (VI), gallium is contained in the place of aluminum and stannoxanes in which, in the general formula (VI), tin is contained in the place of aluminum, whose use as co-catalysts for the polymerization of olefins in the presence of metallocene complexes is known. Further details in relation to said galloxanes and stannoxanes can be found, for example, in U.S. Pat. Nos. 5,128,295 and 5,258,475.

Specific examples of aluminoxanes having general formula (VI) particularly useful for the purpose of the present invention are: methylaluminoxane (MAO), ethyl-aluminoxane, n-butyl-aluminoxane, tetra-iso-butyl-aluminoxane (TIBAO), tert-butyl-aluminoxane, tetra-(2,4,4-tri-methyl-pentyl)-aluminoxane (TIOAO), tetra-(2,3-di-methyl-butyl)-aluminoxane (TDMBAO), tetra-(2,3,3-tri-methyl-butyl)-aluminoxane (TTMBAO). Methylaluminoxane (MAO) is particularly preferred.

Further details on aluminoxanes having general formula (VI) can be found in international patent application WO 2011/061151.

In accordance with a preferred embodiment of the present invention, said compounds or mixtures of compounds ($b_3$) can be selected from organic compounds of aluminum and especially of boron such as, for example, those represented by the following general formulae:

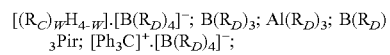

$[(R_C)_wH_{4-w}]\cdot[B(R_D)_4]^-$; $B(R_D)_3$; $Al(R_D)_3$; $B(R_D)_3\text{Pir}$; $[Ph_3C]^+\cdot[B(R_D)_4]^-$;

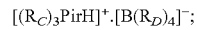

$[(R_C)_3\text{PirH}]^+\cdot[B(R_D)_4]^-$;

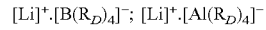

$[Li]^+\cdot[B(R_D)_4]^-$; $[Li]^+\cdot[Al(R_D)_4]^-$ in which w is an integer ranging from 0 to 3, each $R_C$ group independently represents an alkyl group or an aryl group having from 1 to 10 carbon atoms and each $R_D$ group independently represents an aryl group partially or totally, preferably totally fluorinated, having from 6 to 20 carbon atoms, Pir is a pyrrole radical, optionally substituted.

Preferably, when used for the formation of a catalytic (co)polymerization system in accordance with the present invention, the compounds or mixtures of compounds ($b_3$) can be placed in contact with an oxo-nitrogenated iron complex having general formula (I), in proportions such that the molar ratio between the metal (M') contained in the compounds or mixtures of compounds ($b_3$) and the iron contained in the oxo-nitrogenated iron complex having general formula (I) is ranging from 0.1 to 15, preferably ranging from 0.5 to 10, more preferably ranging from 1 to 6. The sequence with which the oxo-nitrogenated iron complex having general formula (I) and the compound or mixture of compounds ($b_3$) are placed in contact with each other is not particularly critical.

Said compounds or mixtures of compounds ($b_3$), especially in the case in which $X_1$ and $X_2$ in the oxo-nitrogenated iron complex having general formula (I) are different from alkyl, must be used in combination with an aluminoxane having general formula (VI) such as, for example, methylaluminoxane (MAO), or, preferably, with an aluminum alkyl having general formula (IV), more preferably a trialkylaluminum having from 1 to 8 carbon atoms in each alkyl residue, such as, for example, tri-methyl-aluminum, tri-ethyl-aluminum, tri-iso-butylaluminum (TIBA).

Examples of the methodologies generally used for the formation of a catalytic (co)polymerization system in accordance with the present invention, in the case of using compounds or mixtures of compounds ($b_3$), are qualitatively depicted in the list reported below, which does not however limit the overall scope of the present invention:

($m_1$) contact of an oxo-nitrogenated iron complex having general formula (I) in which at least one of the X substitutents is an alkyl group, with at least one compound or a mixture of compounds ($b_3$) whose cation is able to react with said alkyl group to form a neutral compound, and whose anion is voluminous, non-coordinating and able to delocalize the negative charge;

($m_2$) reaction of an oxo-nitrogenated iron complex having general formula (I) with at least one aluminum alkyl having general formula (IV), preferably a trialkylaluminum, used in excess molar ratio from 10/1 to 300/1, followed by the reaction with a strong Lewis acid, such as, for example, tris(pentafluorophenyl)boron [compound ($b_3$)], in almost stoichiometric quantities or in slight excess with respect to the iron (Fe);

($m_3$) contact and reaction of an oxo-nitrogenated iron complex having general formula (I) with an excess molar ratio from 10/1 to 1000/1, preferably from 100/1 to 500/1 of at least a trialkylaluminum or an alkyl aluminum halogenide that can be represented with the formula $AlR'''_m Z_{3-m}$ in which R''' is a linear or branched $C_1$-$C_8$ alkyl group, or a mixture thereof, Z is a halogen, preferably chlorine or bromine, and m is a decimal number ranging from 1 to 3, followed by the addition to the composition thus obtained of at least one compound or mixture of compounds ($b_3$) in quantities such that the ratio between said compound or mixture of compounds ($b_3$) or the aluminum of said compound or mixture of compounds ($b_3$) and the iron of the oxo-nitrogenated iron complex having general formula (I) is ranging from 0.1 to 15, preferably from 1 to 6.

Examples of compounds or mixtures of compounds ($b_3$) able to produce an ionic catalytic system by reaction with an oxo-nitrogenated iron complex having general formula (I) according to the present invention are described, although with reference to the formation of ionic metallocene complexes, in the following publications, whose contents are incorporated herein for reference purposes:

Beck W. et al., "*Chemical Reviews*" (1988), Vol. 88, pag. 1405-1421;
Stares S. H., "*Chemical Reviews*" (1993), Vol. 93, pag. 927-942;
European patent applications EP 277 003, EP 495 375, EP 520 732, EP 427 697, EP 421 659, EP 418044;
international patent applications WO 92/00333, WO 92/05208.

Specific examples of compounds or mixtures of compounds ($b_3$) particularly useful for the purpose of the present invention are: tributylammonium-tetrakis-pentafluorophenyl-borate, tributylammonium-tetrakis-pentafluorophenyl-aluminate, tributylammonium-tetrakis-[(3,5-di-(trifluorophenyl)]-borate, tributylammonium-tetrakis-(4-fluorophenyl)]-borate, N,N-dimethylbenzylammonium-tetrakis-pentafluoro-phenyl-borate, N,N-dimethyl-hexylammonium-tetrakis-pentafluorophenyl-borate, N,N-dimethylanilinium-tetrakis-(pentafluorophenyl)-borate, N,N-dimethylanilinium-tetrakis-(pentafluorophenyl)-aluminate, di-(propyl)-ammonium-tetrakis-(pentafluorophenyl)-borate, di-(cyclohexyl)-ammonium-tetrakis-(pentafluorophenyl)-borate, tri-phenyl-carbenium-tetrakis-(pentafluorophenyl)-borate, tri-phenylcarbenium-tetrakis-(penta-fluorophenyl)-aluminate, tris(pentafluorophenyl)borane, tris(pentafluorophenyl)-aluminum, or mixtures thereof. Tetrakis-pentafluorophenyl-borates are preferred.

For the purpose of the present description and of the following claims, the terms "mole" and "molar ratio" are used both with reference to compounds consisting of molecules and with reference to atoms and ions, omitting for the latter ones the terms gram atom or atomic ratio, even if they are scientifically more accurate.

For the purpose of the present invention, other additives or components may potentially be added to the aforementioned catalytic system so as to adapt it to satisfy specific practical requirements. The catalytic systems thus obtained can therefore be considered included within the scope of the present invention. Additives and/or components that can be added in the preparation and/or formulation of the catalytic system according to the present invention are, for example: inert solvents, such as, for example, aliphatic and/or aromatic hydrocarbons; aliphatic and/or aromatic ethers; weakly coordinating additives (e.g. Lewis bases) selected, for example, from non-polymerizable olefins; sterically hindered or electronically poor ethers; halogenating agents such as, for example, silicon halides, halogenated hydrocarbons, preferably chlorinated; or mixtures thereof.

Said catalytic system can be prepared, as already reported above, according to methods known in the prior art.

For example, said catalytic system can be prepared separately (preformed) and subsequently introduced into the (co)polymerization environment. For this purpose, said catalytic system can be prepared by reacting at least one oxo-nitrogenated iron complex (a) having general formula (I) with at least one co-catalyst (b), optionally in the presence of other additives or components selected from those cited above, in the presence of a solvent such as, for example, toluene, heptane, at a temperature ranging from 20° C. to 60° C., for a time ranging from 10 seconds to 10 hours, preferably ranging from 30 seconds to 5 hours. Further details on the preparation of said catalytic system can be found in the examples reported below.

Alternatively, said catalytic system can be prepared in situ, i.e. directly in the (co)polymerization environment. For this purpose, said catalytic system can be prepared by separately introducing the oxo-nitrogenated iron complex (a) having general formula (I), the co-catalyst (b) and the pre-selected conjugated diene(s) to be (co)polymerized, operating at the conditions in which the (co)polymerization is carried out.

For the purpose of the present invention, the aforementioned catalytic systems can also be supported on inert solids, preferably comprising silicon and/or aluminum oxides, such as, for example, silica, alumina or silicoaluminates. For supporting said catalytic systems the known supporting techniques can be used, generally comprising contact, in a suitable inert liquid medium, between the support, optionally activated by heating to temperatures over 200° C., and one or both components (a) and (b) of the catalytic system according to the present invention. It is not necessary, for the purposes of the present invention, for both components to be supported, since only the oxo-nitrogenated iron complex (a) having general formula (I), or the co-catalyst (b) may be present on the support surface. In the latter case, the missing component on the surface is subsequently placed in contact with the supported component when the active catalyst is to be formed by polymerization.

The scope of the present invention also includes the oxo-nitrogenated iron complex having general formula (I), and catalytic systems based thereon, which are supported on a solid through the functionalization of the latter and the formation of a covalent bond between the solid and the oxo-nitrogenated iron complex having general formula (I).

Furthermore, the present invention relates to a (co)polymerization process of conjugated dienes, characterized in that it uses said catalytic system.

The quantity of oxo-nitrogenated iron complex (a) having general formula (I) and co-catalyst (b) which can be used in the (co)polymerization of conjugated dienes varies according to the (co)polymerization process to be carried out. Said quantity is however such as to obtain a molar ratio between the iron contained in the oxo-nitrogenated iron complex having general formula (I) and the metal contained in the co-catalyst (b), e.g., aluminum in the case in which the co-catalyst (b) is selected from the aluminum alkyls ($b_1$) or from the aluminoxanes ($b_2$), boron in the case in which the co-catalyst (b) is selected from the compounds or mixtures of compounds ($b_3$) having general formula (III), comprised between the values reported above.

Specific examples of conjugated dienes that can be (co) polymerized using the catalytic system in accordance with the present invention are: 1,3-butadiene, 2-methyl-1,3-butadiene (isoprene), 2,3-dimethyl-1,3-butadiene, 1,3-pentadiene, 1,3-hexadiene, cyclo-1,3-hexadiene. Preferred (co)polymerizable conjugated dienes are 1,3-butadiene, isoprene. The aforementioned (co)polymerizable conjugated dienes can be used alone, or mixed with two or more dienes. In this latter case, i.e. using a mixture of two or more dienes, a copolymer will be obtained.

In accordance with a particularly preferred embodiment, the present invention relates to a polymerization process of 1,3-butadiene o isoprene, characterized in that it uses said catalytic system.

Generally, said (co)polymerization can be carried out in the presence of a polymerization solvent, generally selected from inert organic solvents, such as, for example: saturated aliphatic hydrocarbons such as, for example, butane, pentane, hexane, heptane, or mixtures thereof; saturated cyclo-aliphatic hydrocarbons such as, for example, cyclopentane, cyclohexane, or mixtures thereof; mono-olefins such as, for example, 1-butene, 2-butene, or mixtures thereof; aromatic hydrocarbons such as, for example, benzene, toluene, xylene, or mixtures thereof; halogenated hydrocarbons such as, for example, methylene chloride, chloroform, carbon tetrachloride, trichloroethylene, perchloroethylene, 1,2-dichloroethane, chlorobenzene, bromobenzene, chlorotoluene, or mixtures thereof. Preferably, the (co)polymerization solvent is selected from saturated aliphatic hydrocarbons.

Alternatively, said (co)polymerization may be performed using as a (co)polymerization solvent the same conjugated diene(s) that must be (co)polymerized, in accordance with the process known as "bulk process".

Generally, the concentration of the conjugated diene to be (co)polymerized in said (co)polymerization solvent is ranging from 5% by weight to 50% by weight, preferably ranging from 10% by weight to 20% by weight, with respect to the total weight of the conjugated diene mixture and inert organic solvent.

Generally, said (co)polymerization can be carried out at a temperature ranging from −70° C. to +100° C., preferably ranging from −20° C. to +80° C.

With regard to pressure, it is preferable to operate at the pressure of the components of the mixture to be (co) polymerized.

Said (co)polymerization can be carried out both continuously and in batches.

As mentioned above, said process allows (co)polymers of conjugated dienes to be obtained, such as, linear or branched polybutadiene or linear or branched polyisoprene, with a mixed structure, in particular polybutadiene with a prevalent 1,4-cis and 1,2 unit content (i.e. having a content of 1,4-cis and 1,2 units≥90%, preferably equal to 100%), and polyisoprene with a prevalent content of 1,4-cis and 3,4 units (i.e. having a content of 1,4-cis and 3,4 units 90%, preferably equal to 100%), which can therefore have different final uses (e.g., use for producing tires or for producing soles for shoes).

For the purpose of understanding the present invention better and to put it into practice, below are some illustrative and non-limiting examples thereof.

EXAMPLES

Reagents and Materials

The list below reports the reagents and materials used in the following examples of the invention, any pre-treatments thereof and their manufacturer:

- iron powder (Fe) (Aldrich): purity 99%, used as such;
- iron (III) chloride ($FeCl_3$) (Aldrich): purity 99.9%, used as such;
- tetrahydrofuran (THF) (Aldrich): used as such;
- iron (II) chloride:tetrahydrofuran complex (1:1.5) [$FeCl_2$($THF$)$_{1.5}$]: prepared from iron powder (Fe) and iron (III) chloride ($FeCl_3$), in tetrahydrofuran (THF) hot, according to the method reported by Calderazzo F. et al., in "Comptes Rendus Académie des Sciences" (1999), t. 2, Série II c, pg. 311-319;
- methylaluminoxane (MAO) (toluene solution 10% by weight) (Chemtura): used as such;
- 2,3-butanedione (Aldrich): used as such;
- aniline (Aldrich): distilled at reduced pressure and stored in an inert atmosphere;
- o-toluidine (Aldrich): distilled at reduced pressure and stored in an inert atmosphere;
- 2-iso-propylaniline (Aldrich): distilled at reduced pressure and stored in an inert atmosphere;
- 2-tert-butylaniline (Aldrich): distilled at reduced pressure and stored in an inert atmosphere;

ethyl ether (Aldrich): pure, ≥99%, distilled over sodium (Na) in an inert atmosphere;

2,6-diethylaniline (Aldrich): distilled at reduced pressure and stored in an inert atmosphere;

2,4,6-tri-methylaniline (Aldrich): distilled at reduced pressure and stored in an inert atmosphere;

toluene (Aldrich): pure, ≥99.5%, distilled over sodium (Na) in an inert atmosphere;

heptane (Aldrich): pure, ≥99%, distilled over sodium (Na) in an inert atmosphere;

sodium sulfate ($Na_2SO_4$) (Aldrich used as such);

1,3-butadiene (Air Liquide): pure, ≥99.5%, evaporated from the container before each production, dried by passing it through a molecular sieve packed column and condensed inside the reactor that was pre-cooled to −20° C.;

isoprene (Aldrich): pure, ≥99%, refluxed over calcium hydride for 2 hours, then distilled "trap-to-trap" and stored in a nitrogen atmosphere at 4° C.;

methanol (Carlo Erba, RPE): used as such;

hydrochloric acid in 37% aqueous solution (Aldrich): used as such;

dichloromethane ($CH_2Cl_2$) (Acros): pure, ≥99.9%, used as such;

hydrofluoric acid (HF) (40% aqueous solution) (Aldrich): used as such;

sulfuric acid ($H_2SO_4$) (96% aqueous solution) (Aldrich): used as such, or diluted with distilled water (1/5);

nitric acid ($HNO_3$) (70% aqueous solution) (Aldrich): used as such;

sodium carbonate ($Na_2CO_3$) (Aldrich): used as such;

silver nitrate ($AgNO_3$) (Aldrich): used as such;

deuterated tetrachloroethylene ($C_2D_2Cl_4$) (Acros): used as such;

hexamethyldisiloxane (HMDS) (Acros): used as such;

deuterated acetone ($C_3D_6O$) (Aldrich): used as such;

tetramethyldisilane (TMS) (Acros): used as such;

The analysis and classification methodologies reported below were used.

Elementary Analysis a) Determination of Fe

For the determination of the quantity by weight of iron (Fe) in the oxo-nitrogenated iron complexes according to the present invention, an exactly weighed aliquot, operating in dry-box under nitrogen flow, of about 30 mg-50 mg of sample, was placed in a 30 ml platinum crucible, together with a 1 ml mixture of 40% hydrofluoric acid (HF), 0.25 ml of 96% sulfuric acid ($H_2SO_4$) and 1 ml of 70% nitric acid ($HNO_3$). The crucible was then heated on a hot plate increasing the temperature until white sulfur fumes appeared (about 200° C.). The mixture thus obtained was cooled to room temperature (20° C.-25° C.) and 1 ml of 70% nitric acid ($HNO_3$) was added, then it was left again until fumes appeared. After repeating the sequence another two times, a clear, almost colorless, solution was obtained. 1 ml of nitric acid ($HNO_3$) and about 15 ml of water were then added cold, then heated to 80° C. for about 30 minutes. The sample thus prepared was diluted with MilliQ pure water until it weighed about 50 g, precisely weighed, to obtain a solution on which the instrumental analytical determination was performed using a Thermo Optek IRIS Advantage Duo ICP-OES (plasma optical emission) spectrometer, for comparison with solutions of known concentration. For this purpose, for every analyte, a calibration curve was prepared in the range 0 ppm-10 ppm, measuring solutions having a known titer obtained by dilution by weight of certified solutions.

The solution of sample prepared as above was then diluted again by weight in order to obtain concentrations close to the reference ones, before performing spectrophotometric measurement. All the samples were prepared in double quantities.

The results were considered acceptable if the individual repeated test data did not have a relative deviation of more than 2% with respect to their mean value.

b) Determination of Chlorine

For said purpose, samples of oxo-nitrogenated iron complexes according to the present invention, about 30 mg-50 mg, were precisely weighed in 100 ml glass beakers in dry-box under nitrogen flow. 2 g of sodium carbonate ($Na_2CO_3$) were added and, outside the dry-box, 50 ml of MilliQ water. It was brought to the boil on the hot plate, under magnetic stirring, for about 30 minutes. It was left to cool, then 1/5 diluted sulfuric acid ($H_2SO_4$) was added, until acid reaction and was then titrated with 0.1 N silver nitrate ($AgNO_3$) with a potentiometric titrator.

c) Determination of Carbon, Hydrogen and Nitrogen

The determination of carbon, hydrogen and nitrogen, in the oxo-nitrogenated iron complexes according to the present invention, as well as in the ligands used for the purpose of the present invention, was performed through a Carlo Erba automatic analyzer Mod. 1106.

$^{13}$C-HMR and $^1$H-HMR Spectra

The $^{13}$C-HMR and $^1$H-HMR spectra were recorded using a nuclear magnetic resonance spectrometer mod. Bruker Avance 400, using deuterated tetrachloroethylene ($C_2D_2Cl_4$) at 103° C., and hexamethyldisiloxane (HDMS) as internal standard, or using deuterated acetone ($C_3D_6O$), at 25° C., and tetramethylsilane (TMS) as internal standard. For this purpose, polymeric solutions were used with concentrations equal to 10% by weight with respect to the total weight of the polymeric solution.

The microstructure of the polymers [i.e. 1,4-cis (%) 1,4-trans (%) and 1,2 (%) unit content for polybutadiene and 1,4-cis (%), 1,4-trans (%) and 3,4 (%) unit content for polyisoprene] was determined through the analysis of the aforementioned spectra based on the contents of literature by Mochel, V. D., in "*Journal of Polymer Science Part A-1: Polymer Chemistry*" (1972), Vol. 10, Issue 4, pg. 1009-1018 for polybutadiene, and by Sato H. et al. in "*Journal of Polymer Science: Polymer Chemistry Edition*" (1979), Vol. 17, Issue 11, pg. 3551-3558, for polyisoprene.

FT-IR Spectra (Solid State—UATR)

The FT-IR spectra (solid state—UATR) were recorded using a Bruker IFS 48 spectrophotometer equipped with a Thermo Spectra-Tech horizontal ATR connection.

The section in which the samples to be analyzed are placed is a Fresnel ATR accessory (Shelton, Conn., USA) which uses crystals of zirconium selenide (ZrSe) with an angle of incidence of 45° in the horizontal direction.

The FT-IR spectra (solid state—UATR) of the oxo-nitrogenated iron complexes according to the present invention, were obtained by inserting samples of the oxo-nitrogenated iron complex to be analyzed into said section.

I.R. Spectra

The FT-IR spectra were recorded through Thermo Nicolet Nexus 670 and Bruker IFS 48 spectrophotometers.

The I.R. spectra (FT-IR) of the ligands used for the purpose of the present invention, were obtained by dispersing the ligand to be analyzed in anhydrous potassium bromide (KBr) (KBr disks), or in Nujol suspension.

The FT-IR spectra of the polymers were obtained from polymeric films on potassium bromide (KBr) tablets, said films being obtained through the deposition of a solution in hot 1,2-dichlorobenzene of the polymer to be analyzed. The concentration of the polymeric solutions analyzed was equal to 10% by weight with respect to the total weight of the polymeric solution.

Determination of the Molecular Weight

The determination of the molecular weight (MW) of the polymers obtained was performed through GPC ("Gel Permeation Chromatography"), using the Waters® Alliance® GPC/V 2000 System by Waters Corporation which uses two detection lines: "Refractive Index"—RI and "Viscometer" operating under the following conditions:

two PLgel Mixed-B columns;
solvent/eluent: o-dichlorobenzene (Aldrich);
flow rate: 0.8 ml/min;
temperature: 145° C.;
molecular mass calculation: Universal Calibration method.

The weight-average molecular weight ($M_w$) and the Polydispersion Index (PDI) corresponding to the ratio $M_w/M_n$ ($M_n$=number-average molecular weight), are reported.

Mass Spectra (GC-MS)

The mass spectra of the ligands used for the purpose of the present invention were performed with a Trace DSQ single quadrupole mass spectrometer (Thermo ISQ) in Electronic Ionization—EI mode, operating under the following conditions:

scanning: from 35 amu to 600 amu (amu=atomic mass unit);
temperature of the source: 250° C.;
transfer line temperature: 300° C.;
capillary column: MDN-5S (Supelco) (length=30 m; diameter=0.25 mm; stationary phase thickness=0.25 μm);
carrier gas: helium (He) with constant flow equal to 1 ml/min.

Example 1

Synthesis of Ligand Having Formula (L1)

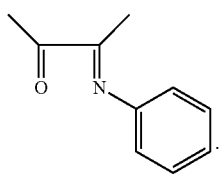

(L1)

The following were loaded into a 250 ml glass reactor, equipped with a magnetic stirrer, in this order: deionized water (50 ml), 2,3-butanedione (28.45 g; 330.5 mmoles) and, by dripping, aniline (10.2 g; 109.5 mmoles). The reaction mixture obtained was left, under stirring, at room temperature, for 2 hours, obtaining the formation of two layered phases, i.e. an organic phase and an aqueous phase. Subsequently, the organic phase was separated from the aqueous phase through a separator funnel, then it was washed, in succession, with deionized water (2×10 ml) and brine (15 ml), anhydrified on sodium sulfate ($Na_2SO_4$), filtered and finally purified by fractional distillation under vacuum using a Vigreux column, obtaining 15 g of a yellow oil (yield=85%) corresponding to the ligand having formula (L1), which was stored, in an inert atmosphere, in the fridge.

Elementary analysis [found (calculated) for $C_{10}H_{11}NO$]: C: 74.47% (74.51%); H: 6.80% (6.88%); N: 8.63% (8.69%).
Molecular weight (MW): 161.20.
GC-MS: $M^+$=m/z 161.
FT-IR (t.q.): 1701 cm$^{-1}$ $v_{(C=O)}$; 1648 cm$^{-1}$ $v_{(C=N)}$.

Example 2

Synthesis of Ligand Having Formula (L2)

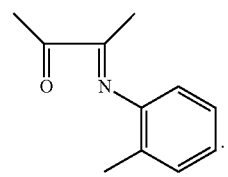

(L2)

The following were loaded into a 250 ml glass reactor, equipped with a magnetic stirrer, in this order: deionized water (50 ml), 2,3-butanedione (24.52 g; 284.8 mmoles) and, by dripping, o-toluidine (10.08 g; 94.07 mmoles). The reaction mixture obtained was left, under stirring, at room temperature, for 2 hours, obtaining the formation of two layered phases, i.e. an organic phase and an aqueous phase. Subsequently, the organic phase was separated from the aqueous phase through a separator funnel, then it was washed, in succession, with deionized water (2×10 ml) and brine (15 ml), anhydrified on sodium sulfate ($Na_2SO_4$), filtered and finally purified by fractional distillation under vacuum using a Vigreux column, obtaining 15.5 g of a yellow oil (yield=94%) corresponding to the ligand having formula (L2), which was stored, in an inert atmosphere, in the fridge.

Elementary analysis [found (calculated) for $C_{11}H_{13}NO$]: C: 74.80% (75.40%); H: 6.96% (7.48%); N: 7.63% (7.99%).
Molecular weight (MW): 175.23.
GC-MS: $M^+$=m/z 175.
FT-IR (t.q.): 1702 cm$^{-1}$ $v_{(C=O)}$; 1647 cm$^{-1}$ $v_{(C=N)}$.

Example 3

Synthesis of Ligand Having Formula (L3)

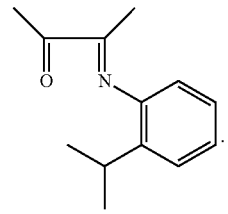

(L3)

The following were loaded into a 250 ml glass reactor, equipped with a magnetic stirrer, in this order: deionized water (70 ml), 2,3-butanedione (19.62 g; 227.9 mmoles) and, by dripping, 2-iso-propylaniline (13.56 g; 100.3 mmoles). The reaction mixture obtained was left, under stirring, at room temperature, for 72 hours, obtaining the formation of two layered phases, i.e. an organic phase and an aqueous phase. Subsequently, the organic phase was separated from the aqueous phase through a separator funnel, then it was washed, in succession, with deionized water (2×10 ml) and brine (15 ml), anhydrified on sodium sulfate (Na$_2$SO$_4$), filtered and finally purified by fractional distillation under vacuum using a Vigreux column, obtaining 20.1 g of a yellow oil (yield=98.6%) corresponding to the ligand having formula (L3), which was stored, in an inert atmosphere, in the fridge.

Elementary analysis [found (calculated) for C$_{13}$H$_{17}$NO]: C: 76.65% (76.81%); H: 8.25% (8.43%); N: 6.89% (6.89%).

Molecular weight (MW): 203.28.

GC-MS: M$^+$=m/z 203.

FT-IR (t.q.): 1702 cm$^{-1}$ $\nu_{(C=O)}$; 1650 cm$^{-1}$ $\nu_{(C=N)}$.

$^1$H-NMR [(C$_3$D$_6$O) δ ppm]: 1,15; 1,16 [both d, 3H each, CH(C$\underline{H}_3$)$_2$]; 1,90; 2,46 (both s, 3H each, CH$_3$); 2,97 [m, 1H, C$\underline{H}$(CH$_3$)$_2$]; 6.61-7.34 (m, 4H, H$_{Ar}$).

Example 4

Synthesis of Ligand Having Formula (L4)

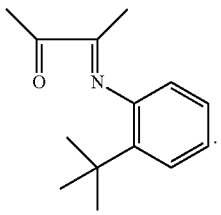

(L4)

The following were loaded into a 250 ml glass reactor, equipped with a magnetic stirrer, in this order: 2,3-butane-dione (19.62 g; 227.9 mmoles), deionized water (70 ml) and, by dripping, 2-tert-butylaniline (15.18 g; 101.7 mmoles). The reaction mixture obtained was left, under stirring, at room temperature, for 24 hours, obtaining the formation of two layered phases, i.e. an organic phase and an aqueous phase.

Subsequently, the organic phase was separated from the aqueous phase through a separator funnel, then it was washed, in succession, with deionized water (2×10 ml) and brine (15 ml), diluted with ethyl ether (20 ml), anhydrified on sodium sulfate (Na$_2$SO$_4$), filtered and finally purified by fractional distillation under vacuum using a Vigreux column, obtaining 21.35 g of a yellow oil (yield=96.6%) corresponding to the ligand having formula (L4), which was stored, in an inert atmosphere, in the fridge.

Elementary analysis [found (calculated) for C$_{14}$H$_{19}$NO]: C: 76.76% (77.38%); H: 8.41% (8.81%); N: 6.28% (6.45%).

Molecular weight (MW): 217.31.

GC-MS: M$^+$=m/z 217.

FT-IR (t.q.): 1702 cm$^{-1}$ $\nu_{(C=O)}$; 1640 cm$^{-1}$ $\nu_{(C=N)}$.

Example 5

Synthesis of Ligand Having Formula (L5)

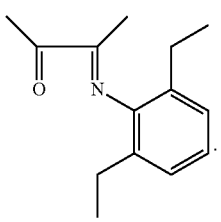

(L5)

The following were loaded into a 250 ml glass reactor, equipped with a magnetic stirrer, in this order: 2,3-butane-dione (14.71 g; 170.9 mmoles), deionized water (80 ml) and, by dripping, 2,6-diethylaniline (12.68 g; 85 mmoles). The reaction mixture obtained was left, under stirring, at room temperature, for 7 days, obtaining the formation of two layered phases, i.e. an organic phase and an aqueous phase.

Subsequently, the organic phase was separated from the aqueous phase through a separator funnel, then it was washed, in succession, with deionized water (2×10 ml) and brine (15 ml), anhydrified on sodium sulfate (Na$_2$SO$_4$), filtered and finally purified by fractional distillation under vacuum using a Vigreux column, obtaining 18.37 g of a yellow oil (yield=99%) corresponding to the ligand having formula (L5), which was stored, in an inert atmosphere, in the fridge.

Elementary analysis [found (calculated) for C$_{14}$H$_{19}$NO]: C: 76.59% (77.38%); H: 8.58% (8.81%); N: 6.23% (6.45%).

Molecular weight (MW): 217.31.

GC-MS: M$^+$=m/z 217.

FT-IR (t.q.): 1704 cm$^{-1}$ $\nu_{(C=O)}$; 1655 cm$^{-1}$ $\nu_{(C=N)}$.

Example 6

Synthesis of Ligand Having Formula (L6)

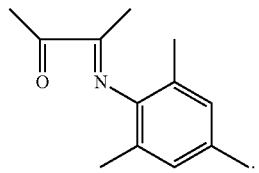

(L6)

The following were loaded into a 250 ml glass reactor, equipped with a magnetic stirrer, in this order: 2,3-butane-dione (7.10 g; 82.4 mmoles), deionized water (40 ml) and, by dripping, 2,4,6-trimethylaniline (5.56 g; 41 mmoles). The reaction mixture obtained was left, under stirring, at room temperature, for 24 hours, obtaining the formation of two layered phases, i.e. an organic phase and an aqueous phase.

Subsequently, the organic phase was separated from the aqueous phase through a separator funnel, then it was washed, in succession, with deionized water (2×10 ml) and brine (15 ml), anhydrified on sodium sulfate (Na$_2$SO$_4$), filtered and finally purified by fractional distillation under vacuum using a Vigreux column, obtaining 7 g of a yellow/orange oil (yield=84%) corresponding to the ligand having formula (L6), which was stored, in an inert atmosphere, in the fridge.

Elementary analysis [found (calculated) for C$_{13}$H$_{17}$NO]: C: 76.76% (76.81%); H: 8.38% (8.53%); N: 6.73% (6.89%).

Molecular weight (MW): 203.28.

GC-MS: M$^+$=m/z 203.

FT-IR (t.q.): 1704 cm$^{-1}$ $\nu_{(C=O)}$; 1647 cm$^{-1}$ $\nu_{(C=N)}$.

Example 7

Synthesis of FeCl$_3$(L1) [Sample MG261]

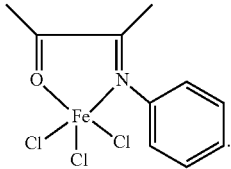

(MG261)

In a 100 ml Schlenk tube, iron (III) chloride (FeCl$_3$) (201 mg; 1.24 mmoles; molar ratio L1/Fe=1) was added to a yellow solution of the ligand having formula (L1) (200 mg; 1.24 mmoles), obtained as described in Example 1, in toluene (20 ml). The mixture obtained was left, under stirring, at room temperature, for 24 hours. The suspension obtained was vacuum dried, at room temperature, and the solid obtained was washed with heptane (2×10 ml) and vacuum dried, at room temperature, obtaining 308 mg of a brown/black solid product corresponding to the complex FeCl$_3$(L1), equal to a 77% conversion with respect to the iron (Ill) chloride (FeCl$_3$) loaded.

Elementary analysis [found (calculated for C$_{10}$H$_{11}$Cl$_3$FeNO)]: C: 36.59% (37.14%); H: 3.02% (3.43%); N: 4.02% (4.33%); Cl: 32.05% (32.89%); Fe: 17.45% (17.27%).

FIG. 1 shows the FT-IR spectrum (solid state—UATR) of the complex FeCl$_3$(L1) obtained.

Example 8

Synthesis of FeCl$_2$(L1) [Sample MG265]

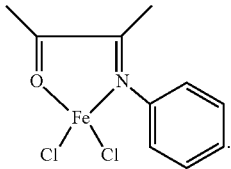

(MG265)

In a 100 ml Schlenk tube, the iron (II) chloride:tetrahydrofuran complex (1:1.5) [FeCl$_2$(THF)$_{1.5}$] (235 mg; 0.97 mmoles; molar ratio L1/Fe=1) was added to a yellow solution of the ligand having formula (L1) (161 mg; 0.99 mmoles), obtained as described in Example 1, in tetrahydrofuran (THF) (20 ml): the mixture obtained was left, under stirring, at room temperature, for 24 hours. The suspension obtained was vacuum dried, at room temperature, and the solid obtained was washed with heptane (2×10 ml) and vacuum dried, at room temperature, obtaining 268 mg of a grey solid product corresponding to the complex FeCl$_2$(L1), equal to a 96% conversion with respect to the iron (II) chloride:tetrahydrofuran complex (1:1.5) [FeCl$_2$(THF)$_{1.5}$] loaded.

Elementary analysis [found (calculated for C$_{10}$H$_{11}$Cl$_2$FeNO)]: C: 41.02% (41.71%); H: 3.59% (3.85%); N: 4.53% (4.86%); Cl: 24.01% (24.62%); Fe: 18.98% (19.39%).

Figure 2:
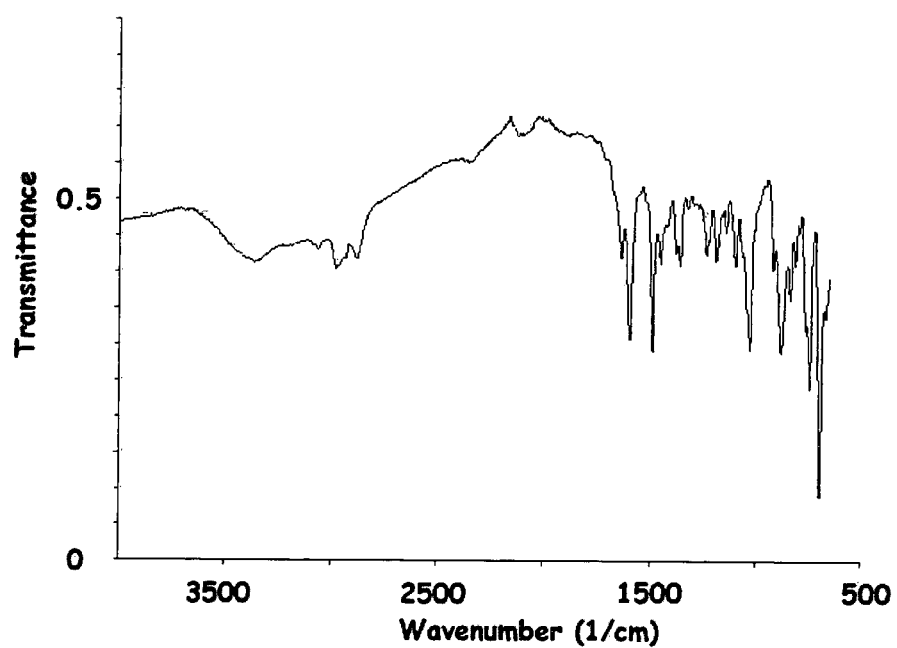
FIG. 2 is the FT-IR spectrum of Example 8.

FIG. 2 shows the FT-IR spectrum (solid state—UATR) of the complex FeCl$_2$(L1) obtained.

Example 9

Synthesis of FeCl$_3$(L2) [Sample MG262]

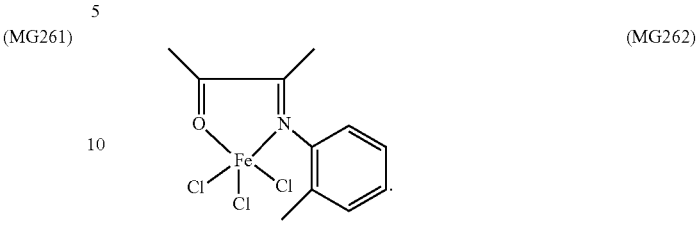

(MG262)

In a 100 ml Schlenk tube, iron (III) chloride (FeCl$_3$) (221 mg; 1.36 mmoles; molar ratio L2/Fe=1) was added to a yellow solution of the ligand having formula (L2) (238 mg; 1.36 mmoles), obtained as described in Example 2, in toluene (20 ml): the mixture obtained was left, under stirring, at room temperature, for 24 hours. The suspension obtained was vacuum dried, at room temperature, and the solid obtained was washed with heptane (2×10 ml) and vacuum dried, at room temperature, obtaining 301 mg of a brown/black solid product corresponding to the complex FeCl$_3$(L2), equal to a 66% conversion with respect to the iron (III) chloride (FeCl$_3$) loaded.

Elementary analysis [found (calculated for C$_{11}$H$_{13}$Cl$_3$FeNO)]: C: 39.46% (39.15%); H: 4.02% (3.88%); N: 4.01% (4.15%); Cl: 31.00% (31.52%); Fe: 16.11% (16.55%).

Figure 3:
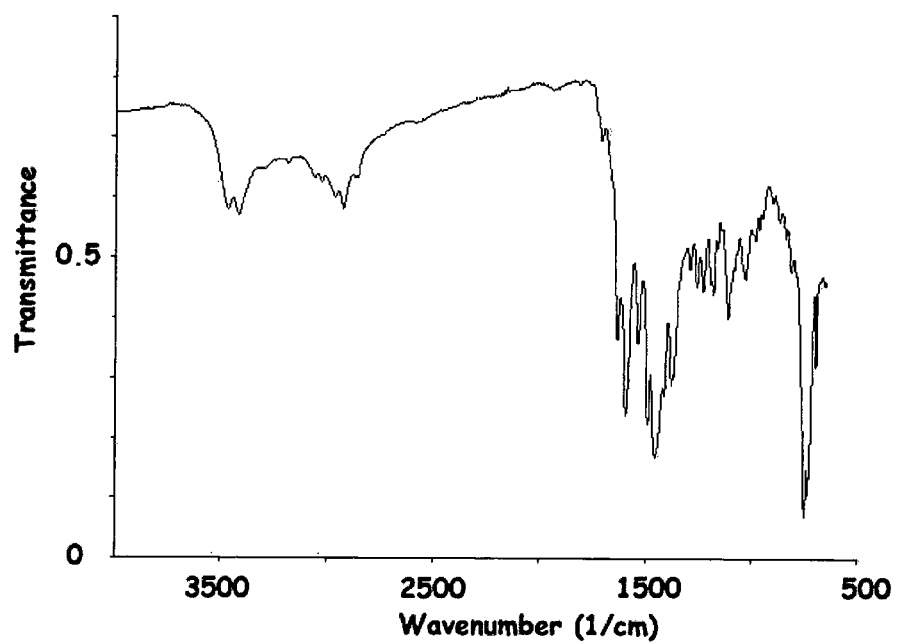
FIG. 3 is the FT-IR spectrum of Example 9.

FIG. 3 shows the FT-IR spectrum (solid state—UATR) of the complex FeCl$_3$(L2) obtained.

Example 10

Synthesis of FeCl$_2$(L2) [Sample MG266]

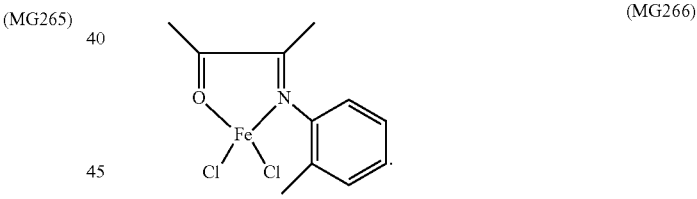

(MG266)

In a 100 ml Schlenk tube, the iron (II) chloride:tetrahydrofuran complex (1:1.5) [FeCl$_2$(THF)$_{1.5}$] (155 mg; 0.64 mmoles; molar ratio L2/Fe=1) was added to a yellow solution of the ligand having formula (L2) (115 mg; 0.66 mmoles), obtained as described in Example 2, in tetrahydrofuran (THF) (20 ml): the mixture obtained was left, under stirring, at room temperature, for 24 hours. The suspension obtained was vacuum dried, at room temperature, and the solid obtained was washed with heptane (2×10 ml) and vacuum dried, at room temperature, obtaining 164 mg of a grey solid product corresponding to the complex FeCl$_2$(L2), equal to a 85% conversion with respect to the iron (II) chloride:tetrahydrofuran complex (1:1.5) [FeCl$_2$(THF)$_{1.5}$] loaded.

Elementary analysis [found (calculated for C$_{11}$H$_{13}$Cl$_2$FeNO)]: C: 43.21% (43.75%); H: 4.01% (4.34%); N: 4.29% (4.64%); Cl: 22.98% (23.48%); Fe: 18.01% (18.49%).

Figure 4:
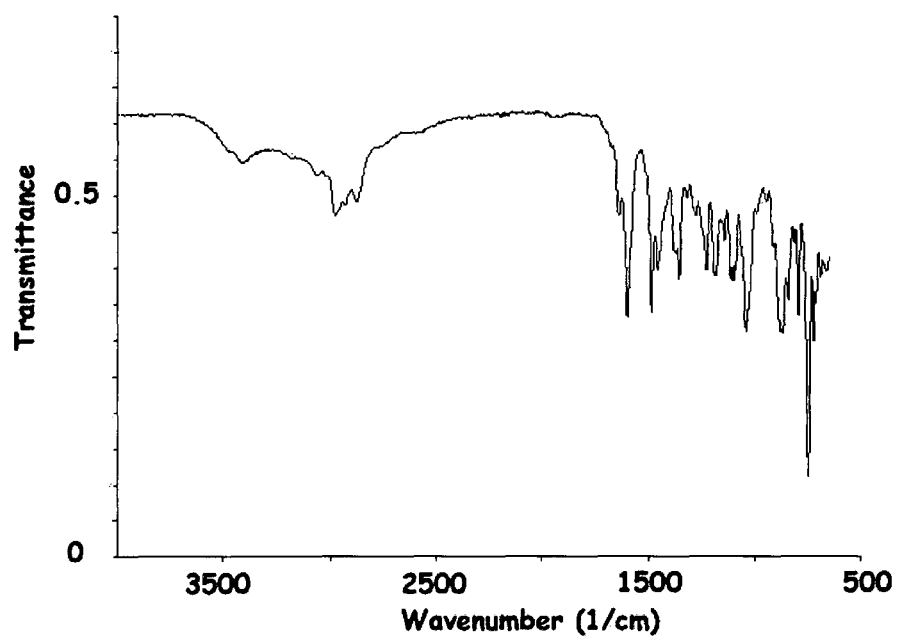
FIG. 4 is the FT-IR spectrum of Example 10.

FIG. 4 shows the FT-IR spectrum (solid state—UATR) of the complex FeCl$_2$(L2) obtained.

Example 11

Synthesis of FeCl₃(L3) [Sample MG267]

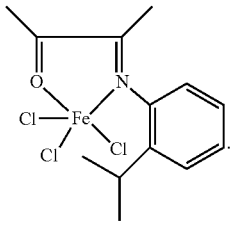

(MG267)

In a 100 ml Schlenk tube, iron (III) chloride (FeCl₃) (328 mg; 2.02 mmoles; molar ratio L3/Fe=1) was added to a yellow solution of the ligand having formula (L3) (411 mg; 2.02 mmoles), obtained as described in Example 3, in toluene (20 ml): the mixture obtained was left, under stirring, at room temperature, for 24 hours. The suspension obtained was vacuum dried, at room temperature, and the solid obtained was washed with heptane (2×10 ml) and vacuum dried, at room temperature, obtaining 528 mg of a brown/black solid product corresponding to the complex FeCl₃(L3), equal to a 72% conversion with respect to the iron (III) chloride (FeCl₃) loaded.

Elementary analysis [found (calculated for $C_{13}H_{17}Cl_3FeNO$)]: C: 42.23% (42.72%); H: 4.51% (4.68%); N: 3.23% (3.83%); Cl: 29.45% (29.10%); Fe: 15.56% (15.28%).

Figure 5:
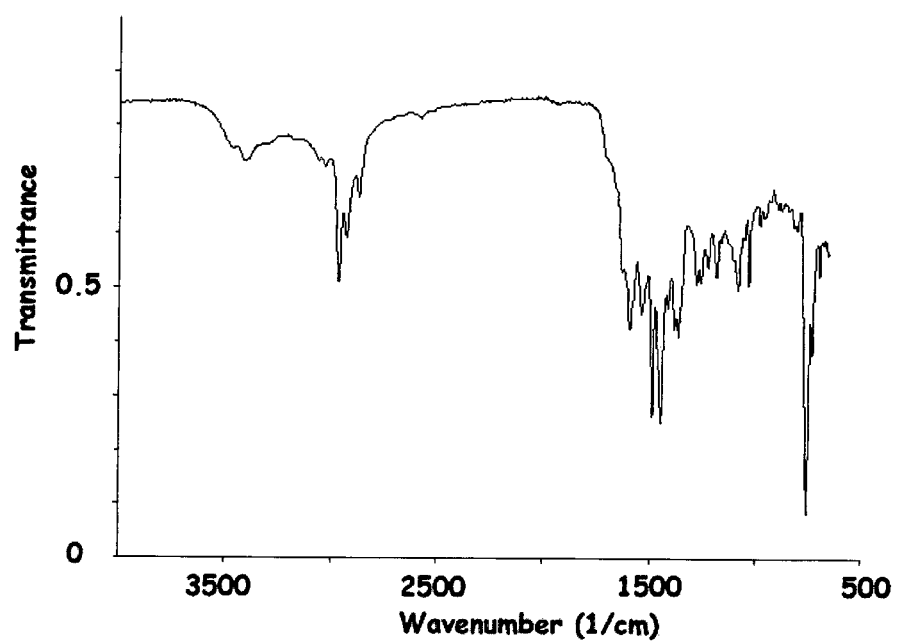
FIG. 5 is the FT-IR spectrum of Example 11.

FIG. 5 shows the FT-IR spectrum (solid state—UATR) of the complex FeCl₃(L3) obtained.

Example 12

Synthesis of FeCl₂(L3) [Sample MG124]

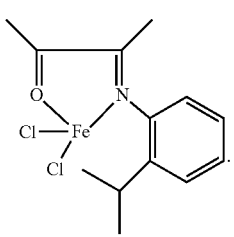

(MG124)

In a 100 ml Schlenk tube, the iron (II) chloride:tetrahydrofuran complex (1:1.5) [FeCl₂(THF)$_{1.5}$] (193 mg; 0.80 mmoles; molar ratio L3/Fe=1) was added to a yellow solution of the ligand having formula (L3) (167 mg; 0.82 mmoles), obtained as described in Example 3, in toluene (30 ml): the mixture obtained was left, under stirring, at 80° C., for 4 hours, obtaining a suspension. The supernatant liquid was discarded and the solid obtained was washed with heptane (2×15 ml) and vacuum dried, at room temperature, obtaining 192 mg of a brown solid product corresponding to the complex FeCl₂(L3), equal to a 73% conversion with respect to the iron (II) chloride:tetrahydrofuran complex (1:1.5) [FeCl₂(THF)$_{1.5}$] loaded.

Elementary analysis [found (calculated for $C_{13}H_{17}Cl_2FeNO$)]: C: 47.85% (47.31%); H: 5.04% (5.19%); N: 4.48% (4.24%); Cl: 21.01% (21.48%); Fe: 16.25% (16.92%).

Figure 6:
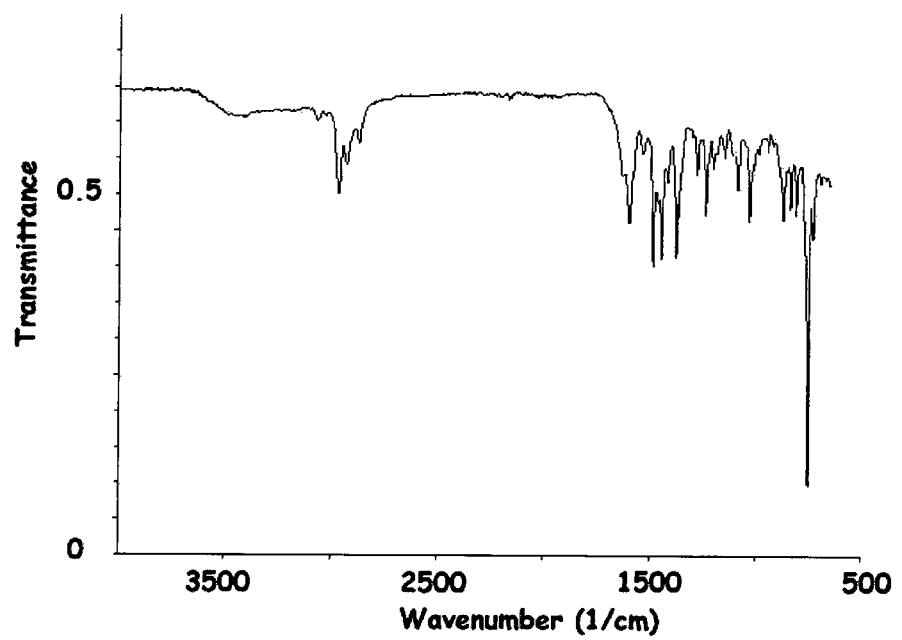
FIG. 6 is the FT-IR spectrum of Example 12.

FIG. 6 shows the FT-IR spectrum (solid state—UATR) of the complex FeCl₂(L3) obtained.

Example 13

Synthesis of FeCl₃(L4) [Sample MG126]

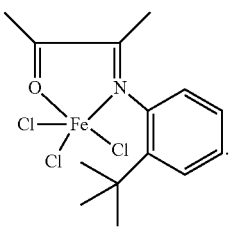

(MG126)

In a 100 ml Schlenk tube, iron (III) chloride (FeCl₃) (102 mg; 0.63 mmoles; molar ratio L4/Fe=1) was added to a yellow solution of the ligand having formula (L4) (135 mg; 0.62 mmoles), obtained as described in Example 4, in toluene (15 ml): the mixture obtained was left, under stirring, at room temperature, for 18 hours, obtaining a suspension. The supernatant liquid was discarded and the solid obtained was washed with heptane (2×15 ml) and vacuum dried, at room temperature, obtaining 179 mg of a brown solid product corresponding to the complex FeCl₃(L4), equal to a 75% conversion with respect to the iron (III) chloride complex (FeCl₃) loaded.

Elementary analysis [found (calculated for $C_{14}H_{19}Cl_3FeNO$)]: C: 44.00% (44.31%); H: 4.95% (5.05%); N: 3.48% (3.69%); Cl: 28.02% (27.58%); Fe: 14.00% (14.71%).

Figure 7:
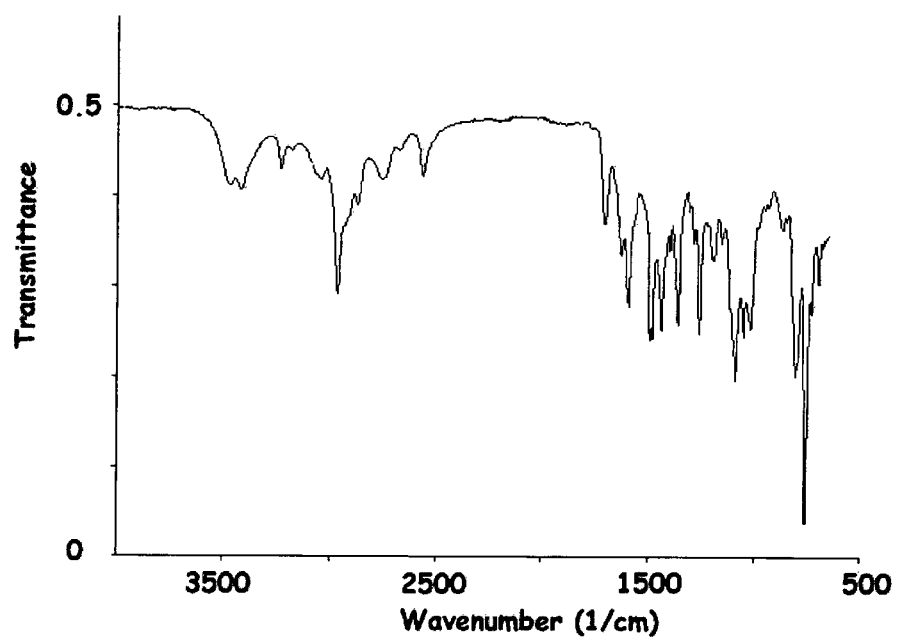
FIG. 7 is the FT-IR spectrum of Example 13.

FIG. 7 shows the FT-IR spectrum (solid state—UATR) of the complex FeCl₃(L4) obtained.

Example 14

Synthesis of FeCl₂(L4) [Sample MG129]

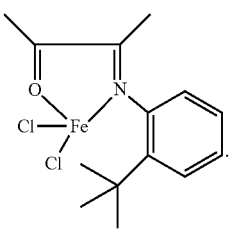

(MG129)

In a 100 ml Schlenk tube, the iron (II) chloride:tetrahydrofuran complex (1:1.5) [FeCl₂(THF)$_{1.5}$] (221 mg; 0.91 mmoles; molar ratio L4/Fe=1) was added to a yellow solution of the ligand having formula (L4) (201 mg; 0.92 mmoles), obtained as described in Example 4, in toluene (20 ml): the mixture obtained was left, under stirring, at 80° C., for 4 hours, obtaining a suspension. The supernatant liquid was discarded and the solid obtained was washed with heptane (2×10 ml) and vacuum dried, at room temperature, obtaining 88 mg of a brown solid product corresponding to the complex FeCl₂(L4), equal to a 28% conversion with respect to the iron (II) chloride:tetrahydrofuran complex (1:1.5) [FeCl₂(THF)$_{1.5}$] loaded.

Elementary analysis [found (calculated for $C_{14}H_{19}Cl_2FeNO$)]: C: 48.00% (48.87%); H: 4.99% (5.56%); N: 3.68% (4.07%); Cl: 20.02% (20.61%); Fe: 16.50% (16.23%).

Figure 8:
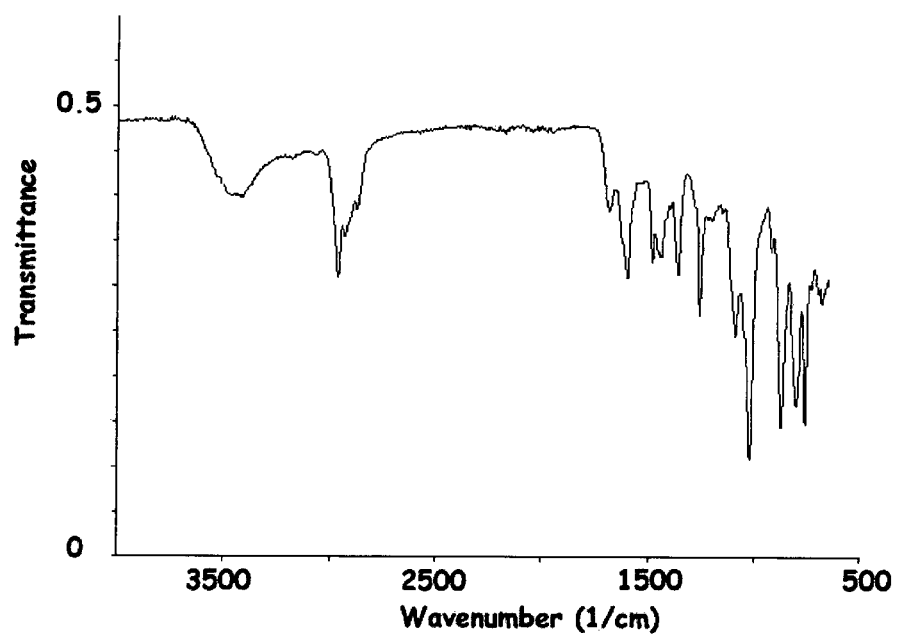
FIG. 8 is the FT-IR spectrum of Example 14.

FIG. 8 shows the FT-IR spectrum (solid state—UATR) of the complex $FeCl_2(L4)$ obtained.

Example 15

Synthesis of $FeCl_3(L5)$ [Sample MG268]

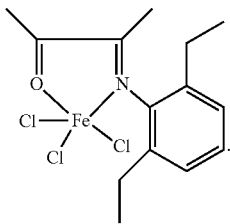

(MG268)

In a 100 ml Schlenk tube, iron (III) chloride ($FeCl_3$) (268 mg; 1.65 mmoles; molar ratio L5/Fe=1) was added to a yellow solution of the ligand having formula (L5) (135 mg; 0.62 mmoles), obtained as described in Example 5, in toluene (20 ml): the mixture obtained was left, under stirring, at room temperature, for 24 hours. The suspension obtained was vacuum dried, at room temperature, and the solid obtained was washed with heptane (2×10 ml) and vacuum dried, at room temperature, obtaining 460 mg of a brown/black solid product corresponding to the complex $FeCl_3(L5)$, equal to a 73% conversion with respect to the iron (III) chloride ($FeCl_3$) loaded.

Elementary analysis [found (calculated for $C_{14}H_{19}Cl_3FeNO$)]: C: 44.01% (44.31%); H: 5.25% (5.04%); N: 3.39% (3.69%); Cl: 27.59% (28.02%); Fe: 14.45% (14.71%).

Figure 9:
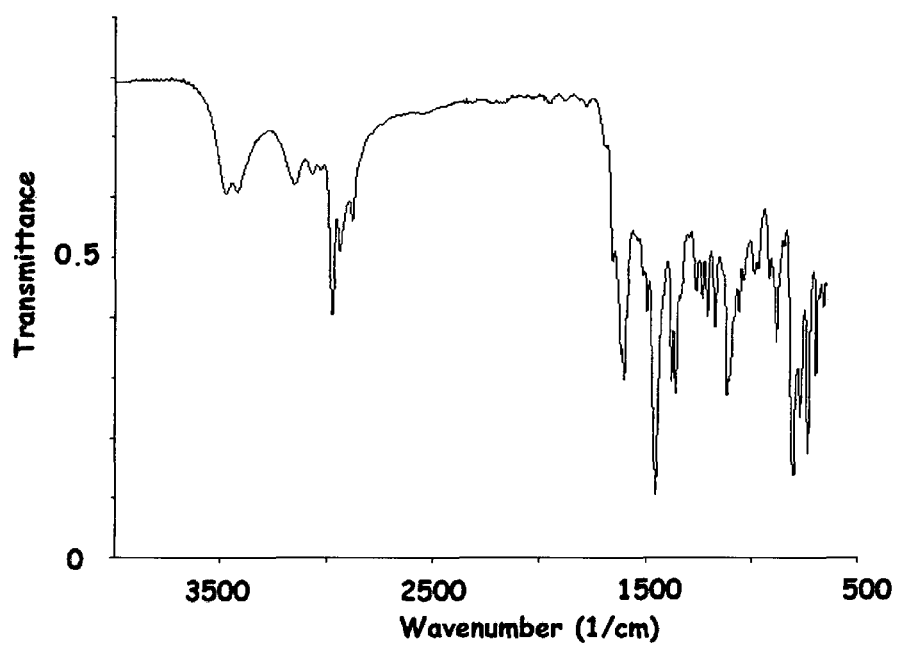
FIG. 9 is the FT-IR spectrum of Example 15.

FIG. 9 shows the FT-IR spectrum (solid state—UATR) of the complex $FeCl_3(L5)$ obtained.

Example 16

Synthesis of $FeCl_2(L5)$ [Sample MG134]

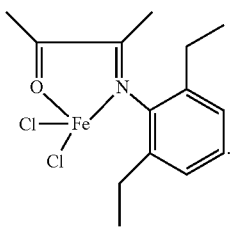

(MG134)

In a 100 ml Schlenk tube, the iron (II) chloride:tetrahydrofuran complex (1:1.5) $[FeCl_2(THF)_{1.5}]$ (233 mg; 0.99 mmoles; molar ratio L5/Fe=1) was added to a yellow solution of the ligand having formula (L5) (214 mg; 0.99 mmoles), obtained as described in Example 5, in toluene (30 ml): the mixture obtained was left, under stirring, at 80° C., for 4 hours, obtaining a suspension. The supernatant liquid was discarded and the solid obtained was washed with heptane (2×15 ml) and vacuum dried, at room temperature, obtaining 279 mg of a brown solid product corresponding to the complex $FeCl_2(L5)$, equal to a 84% conversion with respect to the iron (II) chloride:tetrahydrofuran complex (1:1.5) $[FeCl_2(THF)_{1.5}]$ loaded.

Elementary analysis [found (calculated for $C_{14}H_{19}Cl_2FeNO$)]: C: 48.41% (48.87%); H: 5.02% (5.56%); N: 3.58% (4.07%); Cl: 21.02% (20.61%); Fe: 15.98% (16.23%).

Figure 10:
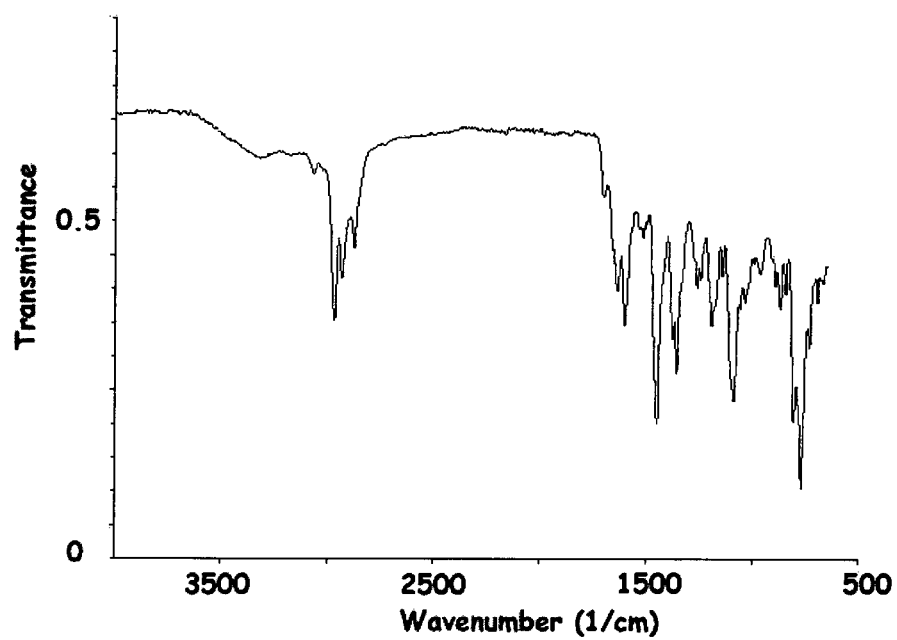
FIG. 10 is the FT-IR spectrum of Example 16.

FIG. 10 shows the FT-IR spectrum (solid state—UATR) of the complex $FeCl_2(L5)$ obtained.

Example 17

Synthesis of $FeCl_3(L6)$ [Sample MG269]

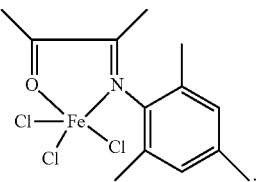

(MG269)

In a 100 ml Schlenk tube, iron (III) chloride ($FeCl_3$) (209 mg; 1.29 mmoles; molar ratio L6/Fe=1) was added to a yellow solution of the ligand having formula (L6) (261 mg; 1.29 mmoles), obtained as described in Example 6, in toluene (20 ml): the mixture obtained was left, under stirring, at room temperature, for 24 hours. The suspension obtained was vacuum dried, at room temperature, and the solid obtained was washed with heptane (2×10 ml) and vacuum dried, at room temperature, obtaining 388 mg of a brown/black solid product corresponding to the complex $FeCl_3(L6)$, equal to a 82% conversion with respect to the iron (III) chloride ($FeCl_3$) loaded.

Elementary analysis [found (calculated for $C_{13}H_{17}Cl_3FeNO$)]: C: 42.31% (42.72%); H: 4.46% (4.68%); N: 3.59% (3.83%); Cl: 29.26% (29.10%); Fe: 15.70% (15.28%).

Figure 11:
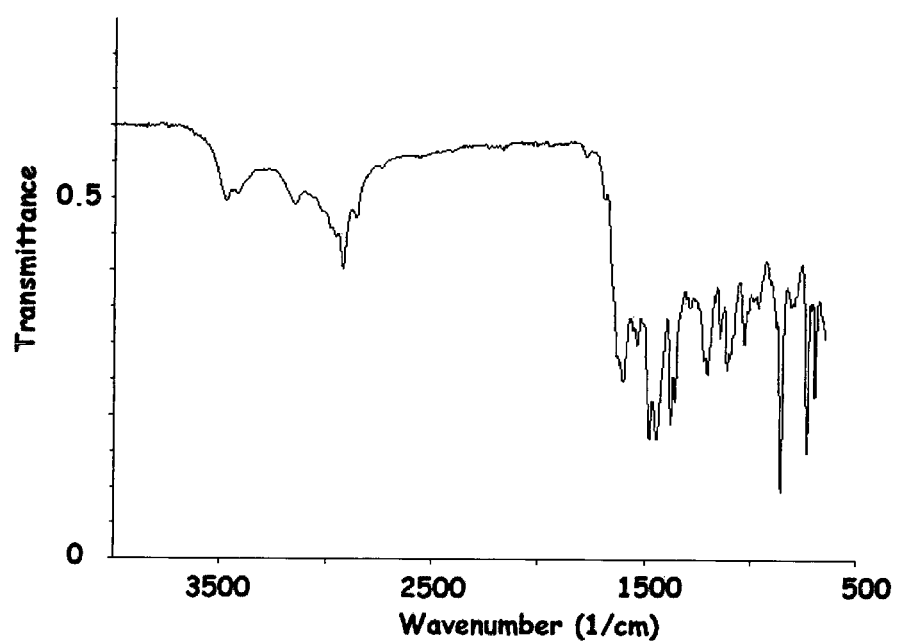
FIG. 11 is the FT-IR spectrum of Example 17.

FIG. 11 shows the FT-IR spectrum (solid state—UATR) of the complex $FeCl_3(L6)$ obtained.

Example 18

Synthesis of $FeCl_2(L6)$ [Sample MG133]

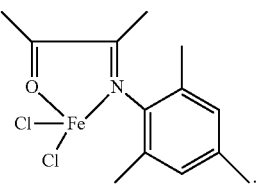

(MG133)

In a 100 ml Schlenk tube, the iron (II) chloride:tetrahydrofuran complex (1:1.5) $[FeCl_2(THF)_{1.5}]$ (356 mg; 1.47 mmoles; molar ratio L6/Fe=1) was added to a yellow solution of the ligand having formula (L6) (308 mg; 1.51 mmoles), obtained as described in Example 6, in toluene (30 ml): the mixture obtained was left, under stirring, at 80° C., for 4 hours, obtaining a suspension. The supernatant liquid was discarded and the solid obtained was washed with heptane (2×15 ml) and vacuum dried, at room temperature, obtaining 380 mg of a brown solid product corresponding to the complex FeCl$_2$(L6), equal to a 78% conversion with respect to the iron (II) chloride:tetrahydrofuran complex (1:1.5) [FeCl$_2$(THF)$_{1.5}$] loaded.

Elementary analysis [found (calculated for C$_{13}$H$_{17}$Cl$_2$FeNO)]: C: 48.01% (47.31%); H: 5.02% (5.19%); N: 4.58% (4.24%); Cl: 21.03% (21.48%); Fe: 16.05% (16.92%).

Figure 12:
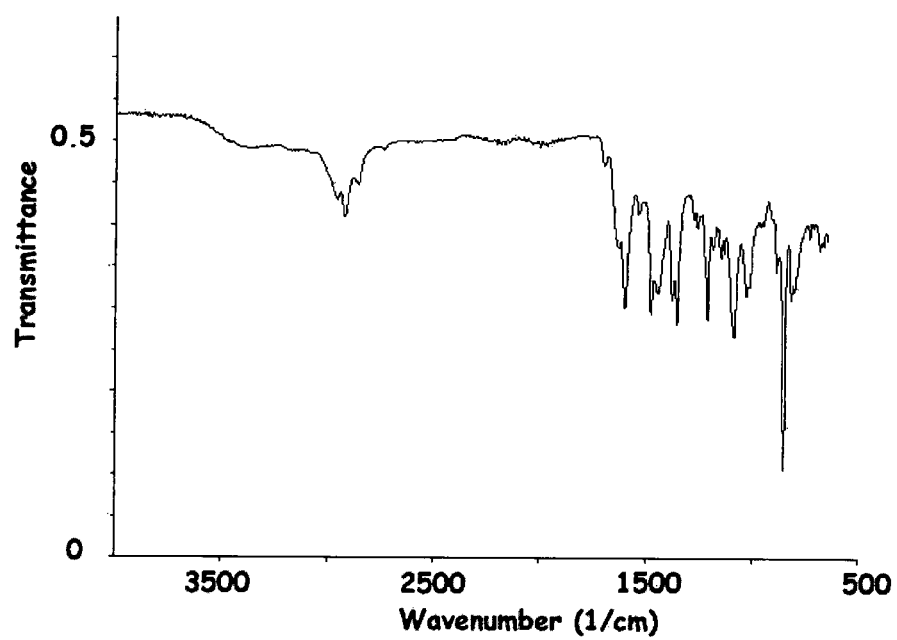
FIG. 12 is the FT-IR spectrum of Example 18.

FIG. 12 shows the FT-IR spectrum (solid state—UATR) of the complex FeCl$_2$(L6) obtained.

Example 19 (G1534)

2 ml of 1,3-butadiene equal to about 1.4 g were condensed, cold (−20° C.), in a 25 ml test tube. Subsequently, 8.1 ml of toluene were added and the temperature of the solution thus obtained was brought to 25° C. Then, methylaluminoxane (MAO) in toluene solution (6.3 ml; 1×10$^{-2}$ moles, equal to about 0.58 g) was added, and, subsequently, the FeCl$_3$(L1) complex [sample MG261] (1.62 ml of toluene solution at concentration of 2 mg/ml; 1×10$^{-5}$ moles, equal to about 3.2 mg) obtained as described in Example 7. Everything was kept under magnetic stirring, at 25° C., for 10 minutes. The polymerization was then stopped by adding 2 ml of methanol containing some drops of hydrochloric acid. The polymer obtained was then coagulated by adding 40 ml of a methanol solution containing 4% of Irganox® 1076 antioxidant (Ciba) obtaining 1.4 g of polybutadiene having a mixed structure: further characteristics of the process and of the polybutadiene obtained are reported in Table 1.

Figure 13:
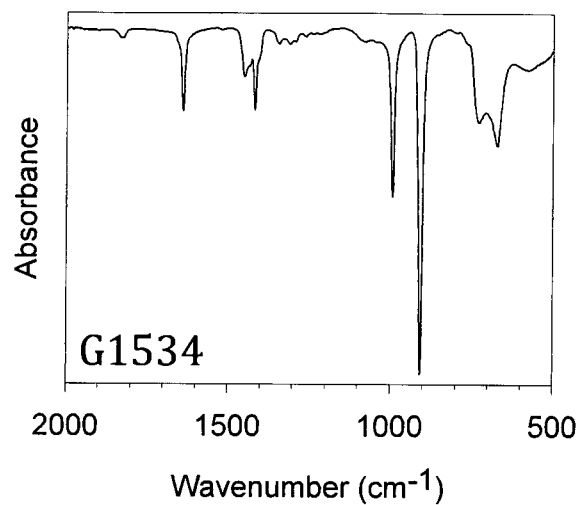
FIG. 13 is the FT-IR spectrum of Example 19.

FIG. 13 shows the FT-IR spectrum of the polybutadiene obtained.

Example 20 (G1535)

2 ml of 1,3-butadiene equal to about 1.4 g were condensed, cold (−20° C.), in a 25 ml test tube. Subsequently, 13.8 ml of toluene were added and the temperature of the solution thus obtained was brought to 25° C. Then, methylaluminoxane (MAO) in toluene solution (0.63 ml; 1×10−3 moles, equal to about 0.058 g) was added, and, subsequently, the FeCl$_3$(L1) complex [sample MG261] (1.62 ml of toluene solution at concentration of 2 mg/ml; 1×10$^5$ moles, equal to about 3.2 mg) obtained as described in Example 7. Everything was kept under magnetic stirring, at 25° C., for 10 minutes. The polymerization was then stopped by adding 2 ml of methanol containing some drops of hydrochloric acid. The polymer obtained was then coagulated by adding 40 ml of a methanol solution containing 4% of Irganox® 1076 antioxidant (Ciba) obtaining 1.14 g of polybutadiene having a mixed structure: further characteristics of the process and of the polybutadiene obtained are reported in Table 1.

Figure 14:
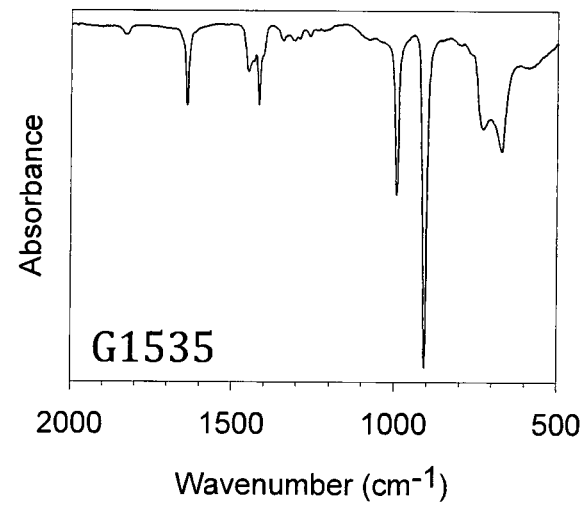
FIG. 14 is the FT-IR spectrum of Example 20.

FIG. 14 shows the FT-IR spectrum of the polybutadiene obtained.

Example 21 (G1536)

2 ml of 1,3-butadiene equal to about 1.4 g were condensed, cold (−20° C.), in a 25 ml test tube. Subsequently, 14.3 ml of toluene were added and the temperature of the solution thus obtained was brought to 25° C. Then, methylaluminoxane (MAO) in toluene solution (0.063 ml; 1×10$^{-4}$ moles, equal to about 0.0058 g) was added, and, subsequently, the FeCl$_3$(L1) complex [sample MG261] (1.62 ml of toluene solution at concentration of 2 mg/ml; 1×10$^{-5}$ moles, equal to about 3.2 mg) obtained as described in Example 7. Everything was kept under magnetic stirring, at 25° C., for 20 minutes. The polymerization was then stopped by adding 2 ml of methanol containing some drops of hydrochloric acid. The polymer obtained was then coagulated by adding 40 ml of a methanol solution containing 4% of Irganox® 1076 antioxidant (Ciba) obtaining 1.4 g of polybutadiene having a mixed structure: further characteristics of the process and of the polybutadiene obtained are reported in Table 1.

Figure 15:
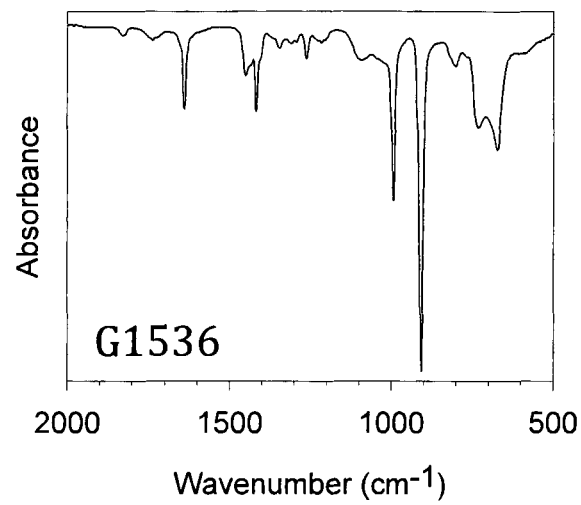
FIG. 15 is the FT-IR spectrum of Example 21.

FIG. 15 shows the FT-IR spectrum of the polybutadiene obtained.

Example 22 (G1535/1)

2 ml of 1,3-butadiene equal to about 1.4 g were condensed, cold (−20° C.), in a 25 ml test tube. Subsequently, 13.9 ml of toluene were added and the temperature of the solution thus obtained was brought to 25° C. Then, methylaluminoxane (MAO) in toluene solution (0.63 ml; 1×10$^{-3}$ moles, equal to about 0.058 g) was added, and, subsequently, the FeCl$_2$(L1) complex [sample MG265] (1.45 ml of toluene solution at concentration of 2 mg/ml; 1×10$^{-5}$ moles, equal to about 2.9 mg) obtained as described in Example 8. Everything was kept under magnetic stirring, at 25° C., for 15 minutes. The polymerization was then stopped by adding 2 ml of methanol containing some drops of hydrochloric acid. The polymer obtained was then coagulated by adding 40 ml of a methanol solution containing 4% of Irganox® 1076 antioxidant (Ciba) obtaining 1.4 g of polybutadiene having a mixed structure: further characteristics of the process and of the polybutadiene obtained are reported in Table 1.

Figure 16:
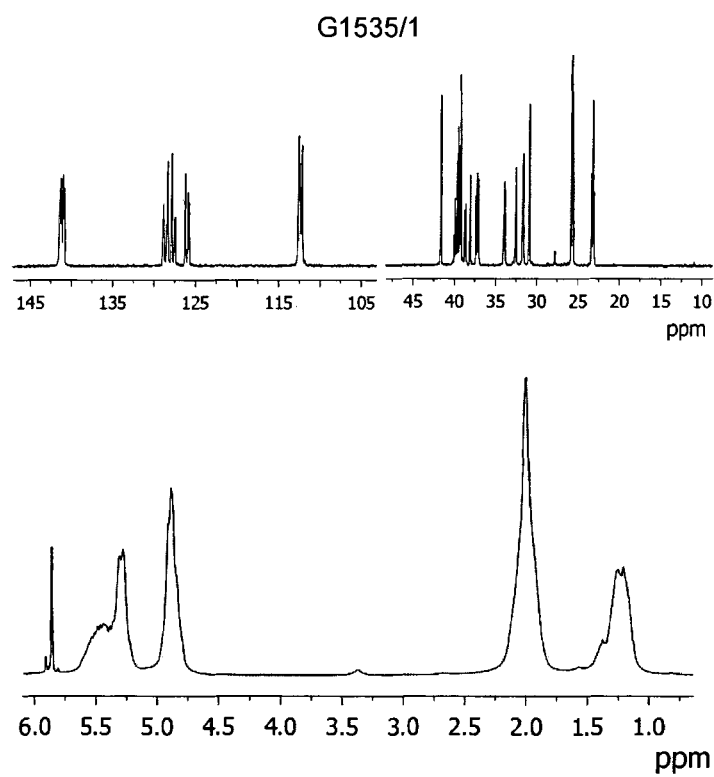
FIG. 16 is the $^1$H-NMR and $^{13}$C-NMR spectra of Example 22.

FIG. 16 shows the $^1$H-NMR (top) and $^{13}$C-NMR (bottom) spectra of the polybutadiene obtained.

Example 23 (G1537)

2 ml of 1,3-butadiene equal to about 1.4 g were condensed, cold (−20° C.), in a 25 ml test tube. Subsequently, 8 ml of toluene were added and the temperature of the solution thus obtained was brought to 25° C. Then, methylaluminoxane (MAO) in toluene solution (6.3 ml; 1×10$^{-2}$ moles, equal to about 0.58 g) was added, and, subsequently, the FeCl$_3$(L2) complex [sample MG262] (1.7 ml of toluene solution at concentration of 2 mg/ml; 1×10$^{-5}$ moles, equal to about 3.4 mg) obtained as described in Example 9. Everything was kept under magnetic stirring, at 25° C., for 120 minutes. The polymerization was then stopped by adding 2 ml of methanol containing some drops of hydrochloric acid. The polymer obtained was then coagulated by adding 40 ml of a methanol solution containing 4% of Irganox® 1076 antioxidant (Ciba) obtaining 0.989 g of polybutadiene having a mixed structure: further characteristics of the process and of the polybutadiene obtained are reported in Table 1.

Figure 17:
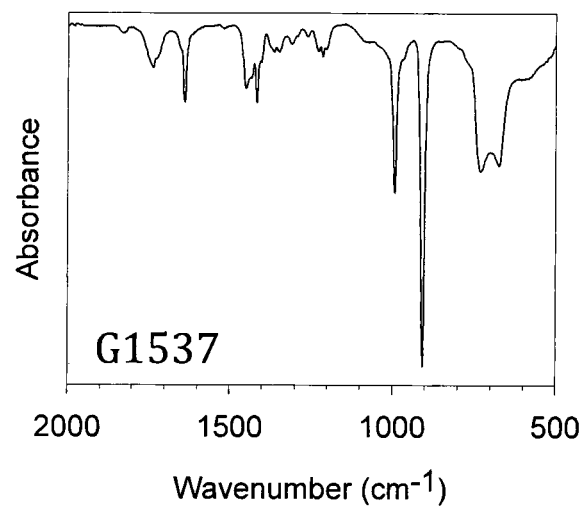
FIG. 17 is the FT-IR spectrum of Example 23.

FIG. 17 shows the FT-IR spectrum of the polybutadiene obtained.

Example 24 (G1538)

2 ml of 1,3-butadiene equal to about 1.4 g were condensed, cold (−20° C.), in a 25 ml test tube. Subsequently, 13.7 ml of toluene were added and the temperature of the solution thus obtained was brought to 25° C. Then, methylaluminoxane (MAO) in toluene solution (0.63 ml; 1×10$^{-3}$ moles, equal to about 0.058 g) was added, and, subsequently, the FeCl$_3$(L2) complex [sample MG262] (1.7 ml of toluene solution at concentration of 2 mg/ml; 1×10$^{-5}$ moles, equal to about 3.4 mg) obtained as described in Example 9. Everything was kept under magnetic stirring, at 25° C., for 120 minutes. The polymerization was then stopped by adding 2 ml of methanol containing some drops of hydrochloric acid. The polymer obtained was then coagulated by adding 40 ml of a methanol solution containing 4% of Irganox® 1076 antioxidant (Ciba) obtaining 0.922 g of polybutadiene having a mixed structure: further characteristics of the process and of the polybutadiene obtained are reported in Table 1.

Figure 18:
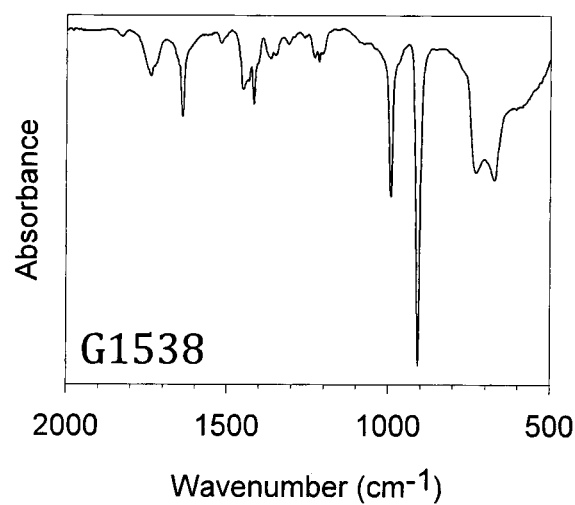
FIG. 18 is the FT-IR spectrum of Example 24.

FIG. 18 shows the FT-IR spectrum of the polybutadiene obtained.

Example 25 (G1539)

2 ml of 1,3-butadiene equal to about 1.4 g were condensed, cold (−20° C.), in a 25 ml test tube. Subsequently, 14.1 ml of toluene were added and the temperature of the solution thus obtained was brought to 25° C. Then, methylaluminoxane (MAO) in toluene solution (0.16 ml; $2.5 \times 10^{-4}$ moles, equal to about 0.0145 g) was added, and, subsequently, the $FeCl_3(L2)$ complex [sample MG262] (1.7 ml of toluene solution at concentration of 2 mg/ml; $1 \times 10^{-5}$ moles, equal to about 3.4 mg) obtained as described in Example 9. Everything was kept under magnetic stirring, at 25° C., for 420 minutes. The polymerization was then stopped by adding 2 ml of methanol containing some drops of hydrochloric acid. The polymer obtained was then coagulated by adding 40 ml of a methanol solution containing 4% of Irganox® 1076 antioxidant (Ciba) obtaining 0.434 g of polybutadiene having a mixed structure: further characteristics of the process and of the polybutadiene obtained are reported in Table 1.

Figure 19:
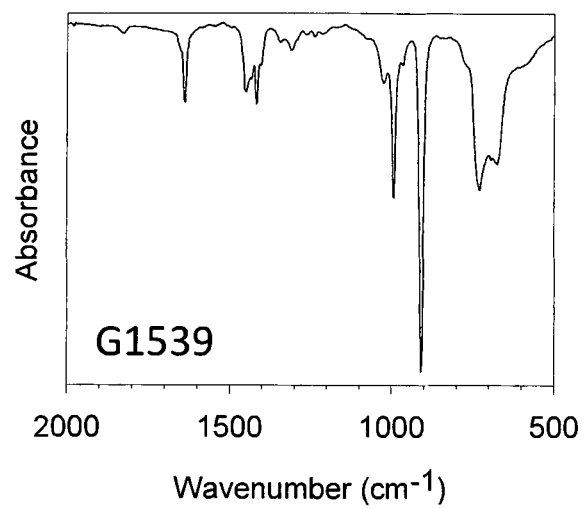
FIG. 19 is the FT-IR spectrum of Example 25.

FIG. 19 shows the FT-IR spectrum of the polybutadiene obtained.

Example 26 (G1539/1)

2 ml of 1,3-butadiene equal to about 1.4 g were condensed, cold (−20° C.), in a 25 ml test tube. Subsequently, 14.3 ml of toluene were added and the temperature of the solution thus obtained was brought to 25° C. Then, methylaluminoxane (MAO) in toluene solution (0.16 ml; $2.5 \times 10^{-4}$ moles, equal to about 0.0145 g) was added, and, subsequently, the $FeCl_2(L2)$ complex [sample MG266] (1.5 ml of toluene solution at concentration of 2 mg/ml; $1 \times 10^{-5}$ moles, equal to about 3 mg) obtained as described in Example 10. Everything was kept under magnetic stirring, at 25° C., for 600 minutes. The polymerization was then stopped by adding 2 ml of methanol containing some drops of hydrochloric acid. The polymer obtained was then coagulated by adding 40 ml of a methanol solution containing 4% of Irganox® 1076 antioxidant (Ciba) obtaining 0.690 g of polybutadiene having a mixed structure: further characteristics of the process and of the polybutadiene obtained are reported in Table 1.

Figure 20:
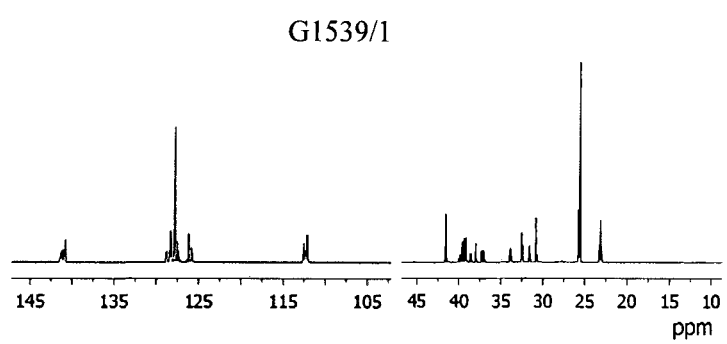
FIG. 20 is the $^1$H-NMR and $^{13}$C-NMR spectra of Example 26.
Figure 20:
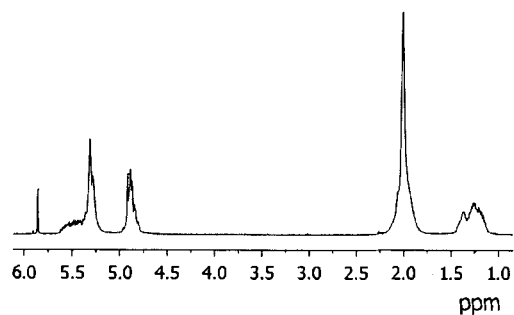

FIG. 20 shows the $^1$H-NMR (top) and $^{13}$C-NMR (bottom) spectra of the polybutadiene obtained.

Example 27 (IP121/1)

2 ml of 1,3-butadiene equal to about 1.4 g were condensed, cold (−20° C.), in a 25 ml test tube. Subsequently, 7.9 ml of toluene were added and the temperature of the solution thus obtained was brought to 25° C. Then, methylaluminoxane (MAO) in toluene solution (6.3 ml; $1 \times 10^{-2}$ moles, equal to about 0.58 g) was added, and, subsequently, the $FeCl_3(L3)$ complex [sample MG267] (1.83 ml of toluene solution at concentration of 2 mg/ml; $1 \times 10^{-5}$ moles, equal to about 3.65 mg) obtained as described in Example 11. Everything was kept under magnetic stirring, at 25° C., for 180 minutes. The polymerization was then stopped by adding 2 ml of methanol containing some drops of hydrochloric acid. The polymer obtained was then coagulated by adding 40 ml of a methanol solution containing 4% of Irganox® 1076 antioxidant (Ciba) obtaining 0.694 g of polybutadiene having a mixed structure: further characteristics of the process and of the polybutadiene obtained are reported in Table 1.

Figure 21:
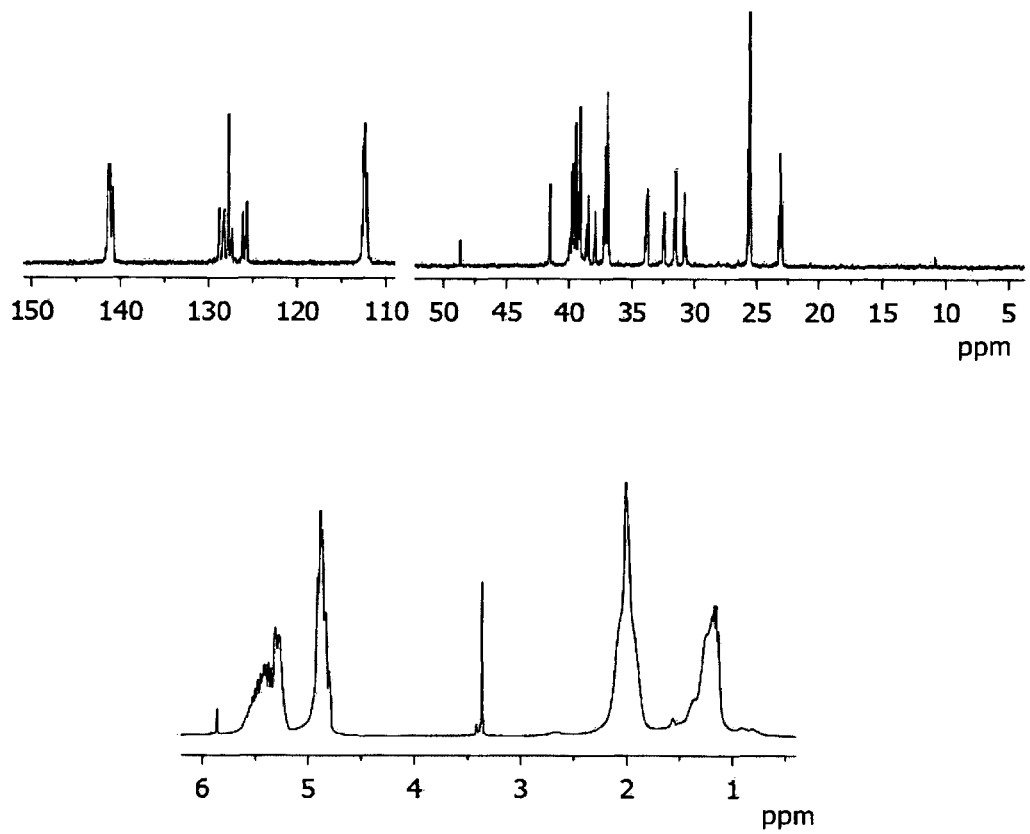
FIG. 21 is the $^1$H-NMR and $^{13}$C-NMR spectra of Example 27.

FIG. 21 shows the $^1$H-NMR (top) and $^{13}$C-NMR (bottom) spectra of the polybutadiene obtained.

Example 28 (IP121)

2 ml of 1,3-butadiene equal to about 1.4 g were condensed, cold (−20° C.), in a 25 ml test tube. Subsequently, 8 ml of toluene were added and the temperature of the solution thus obtained was brought to 25° C. Then, methylaluminoxane (MAO) in toluene solution (6.3 ml; $1 \times 10^{-2}$ moles, equal to about 0.58 g) was added, and, subsequently, the $FeCl_2(L3)$ complex [sample MG124] (1.65 ml of toluene solution at concentration of 2 mg/ml; $1 \times 10^{-5}$ moles, equal to about 3.3 mg) obtained as described in Example 12. Everything was kept under magnetic stirring, at 25° C., for 180 minutes. The polymerization was then stopped by adding 2 ml of methanol containing some drops of hydrochloric acid. The polymer obtained was then coagulated by adding 40 ml of a methanol solution containing 4% of Irganox® 1076 antioxidant (Ciba) obtaining 0.737 g of polybutadiene having a mixed structure: further characteristics of the process and of the polybutadiene obtained are reported in Table 1.

Figure 22:
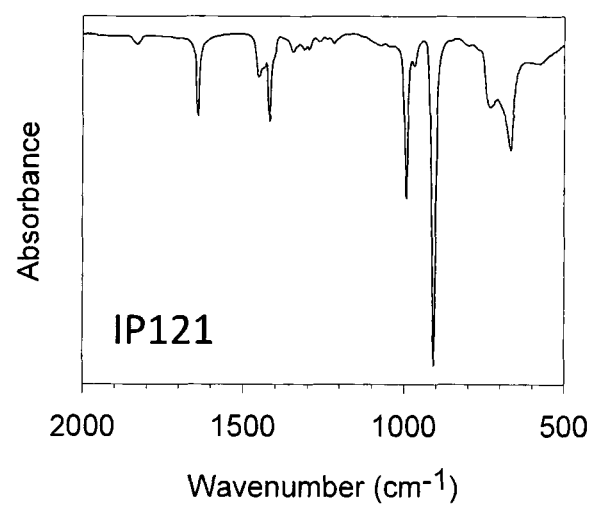
FIG. 22 is the FT-IR spectrum of Example 28.

FIG. 22 shows the FT-IR spectrum of the polybutadiene obtained.

Example 29 (IP124)

2 ml of 1,3-butadiene equal to about 1.4 g were condensed, cold (−20° C.), in a 25 ml test tube. Subsequently, 7.8 ml of toluene were added and the temperature of the solution thus obtained was brought to 25° C. Then, methylaluminoxane (MAO) in toluene solution (6.3 ml; $1 \times 10^{-2}$ moles, equal to about 0.58 g) was added, and, subsequently, the $FeCl_3(L4)$ complex [sample MG126] (1.9 ml of toluene solution at concentration of 2 mg/ml; $1 \times 10^{-5}$ moles, equal to about 3.8 mg) obtained as described in Example 13. Everything was kept under magnetic stirring, at 25° C., for 1380 minutes. The polymerization was then stopped by adding 2 ml of methanol containing some drops of hydrochloric acid. The polymer obtained was then coagulated by adding 40 ml of a methanol solution containing 4% of Irganox® 1076 antioxidant (Ciba) obtaining 0.368 g of polybutadiene having a mixed structure: further characteristics of the process and of the polybutadiene obtained are reported in Table 1.

Figure 23:
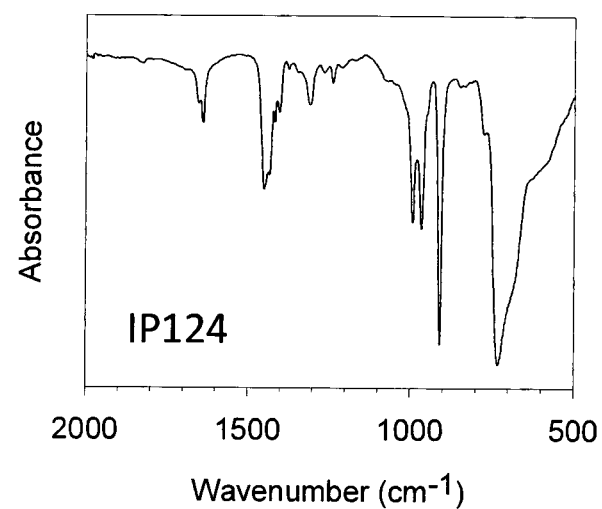
FIG. 23 is the FT-IR spectrum of Example 29.

FIG. 23 shows the FT-IR spectrum of the polybutadiene obtained.

Example 30 (IP122)

2 ml of 1,3-butadiene equal to about 1.4 g were condensed, cold (−20° C.), in a 25 ml test tube. Subsequently, 8 ml of toluene were added and the temperature of the solution thus obtained was brought to 25° C. Then, methylaluminoxane (MAO) in toluene solution (6.3 ml; $1 \times 10^{-2}$ moles, equal to about 0.58 g) was added, and, subsequently, the $FeCl_2(L4)$ complex [sample MG129] (1.7 ml of toluene solution at concentration of 2 mg/ml; $1 \times 10^{-5}$ moles, equal to about 3.4 mg) obtained as described in Example 14. Everything was kept under magnetic stirring, at 25° C., for 2880 minutes. The polymerization was then stopped by adding 2 ml of methanol containing some drops of hydrochloric acid. The polymer obtained was then coagulated by adding 40 ml of a methanol solution containing 4% of Irganox® 1076 antioxidant (Ciba) obtaining 0.651 g of polybutadiene having a mixed structure: further characteristics of the process and of the polybutadiene obtained are reported in Table 1.

Figure 24:
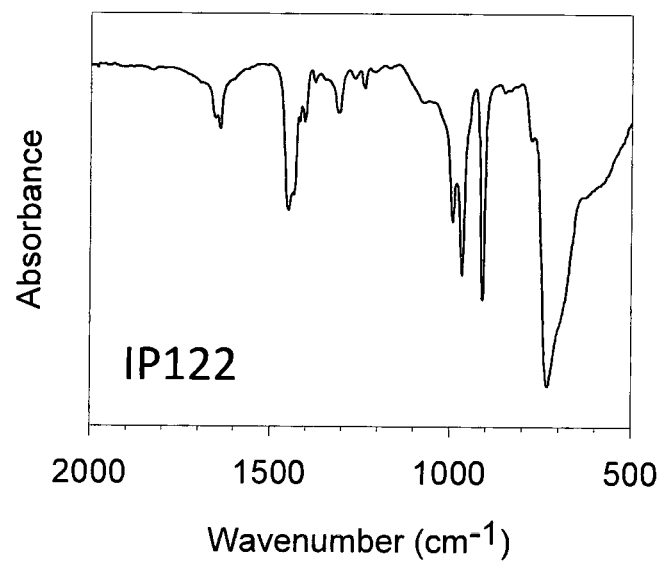
FIG. 24 is the FT-IR spectrum of Example 30.

FIG. 24 shows the FT-IR spectrum of the polybutadiene obtained.

Example 31 (IP123)

2 ml of 1,3-butadiene equal to about 1.4 g were condensed, cold (−20° C.), in a 25 ml test tube. Subsequently, 8 ml of toluene were added and the temperature of the solution thus obtained was brought to 25° C. Then, methylaluminoxane (MAO) in toluene solution (6.3 ml; $1\times10^{-2}$ moles, equal to about 0.58 g) was added, and, subsequently, the $FeCl_2$(L5) complex [sample MG134] (1.7 ml of toluene solution at concentration of 2 mg/ml; $1\times10^{-5}$ moles, equal to about 3.4 mg) obtained as described in Example 16. Everything was kept under magnetic stirring, at 25° C., for 1680 minutes. The polymerization was then stopped by adding 2 ml of methanol containing some drops of hydrochloric acid. The polymer obtained was then coagulated by adding 40 ml of a methanol solution containing 4% of Irganox® 1076 antioxidant (Ciba) obtaining 0.179 g of polybutadiene having a mixed structure: further characteristics of the process and of the polybutadiene obtained are reported in Table 1.

Figure 25:
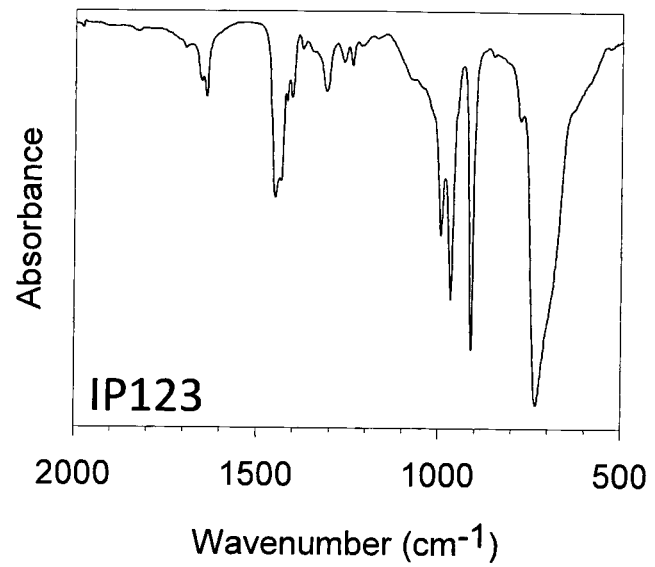
FIG. 25 is the FT-IR spectrum of Example 31.

FIG. 25 shows the FT-IR spectrum of the polybutadiene obtained.

Example 32 (IP123/1)

2 ml of 1,3-butadiene equal to about 1.4 g were condensed, cold (−20° C.), in a 25 ml test tube. Subsequently, 7.8 ml of toluene were added and the temperature of the solution thus obtained was brought to 25° C. Then, methylaluminoxane (MAO) in toluene solution (6.3 ml; $1\times10^{-2}$ moles, equal to about 0.58 g) was added, and, subsequently, the $FeCl_3$(L5) complex [sample MG268] (1.9 ml of toluene solution at concentration of 2 mg/ml; $1\times10^{-5}$ moles, equal to about 3.8 mg) obtained as described in Example 15. Everything was kept under magnetic stirring, at 25° C., for 1680 minutes. The polymerization was then stopped by adding 2 ml of methanol containing some drops of hydrochloric acid. The polymer obtained was then coagulated by adding 40 ml of a methanol solution containing 4% of Irganox® 1076 antioxidant (Ciba) obtaining 0.248 g of polybutadiene having a mixed structure: further characteristics of the process and of the polybutadiene obtained are reported in Table 1.

Figure 26:
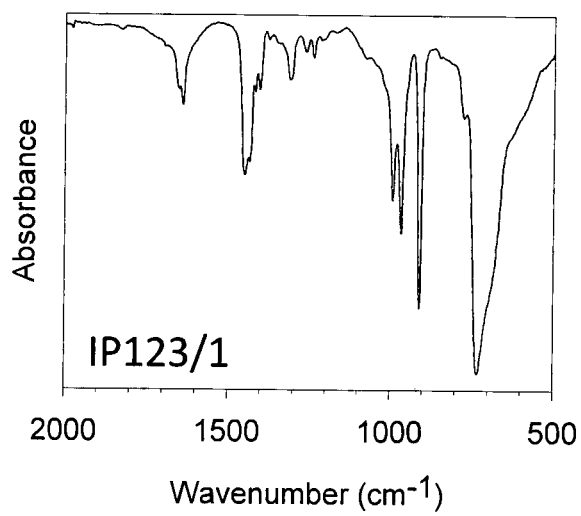
FIG. 26 is the FT-IR spectrum of Example 32.

FIG. 26 shows the FT-IR spectrum of the polybutadiene obtained.

Example 33 (IP125)

2 ml of 1,3-butadiene equal to about 1.4 g were condensed, cold (−20° C.), in a 25 ml test tube. Subsequently, 8.1 ml of toluene were added and the temperature of the solution thus obtained was brought to 25° C. Then, methylaluminoxane (MAO) in toluene solution (6.3 ml; $1\times10^{-2}$ moles, equal to about 0.58 g) was added, and, subsequently, the $FeCl_2$(L6) complex [sample MG133] (1.65 ml of toluene solution at concentration of 2 mg/ml; $1\times10^{-5}$ moles, equal to about 3.3 mg) obtained as described in Example 18. Everything was kept under magnetic stirring, at 25° C., for 5760 minutes. The polymerization was then stopped by adding 2 ml of methanol containing some drops of hydrochloric acid. The polymer obtained was then coagulated by adding 40 ml of a methanol solution containing 4% of Irganox® 1076 antioxidant (Ciba) obtaining 0.152 g of polybutadiene having a mixed structure: further characteristics of the process and of the polybutadiene obtained are reported in Table 1.

Figure 27:
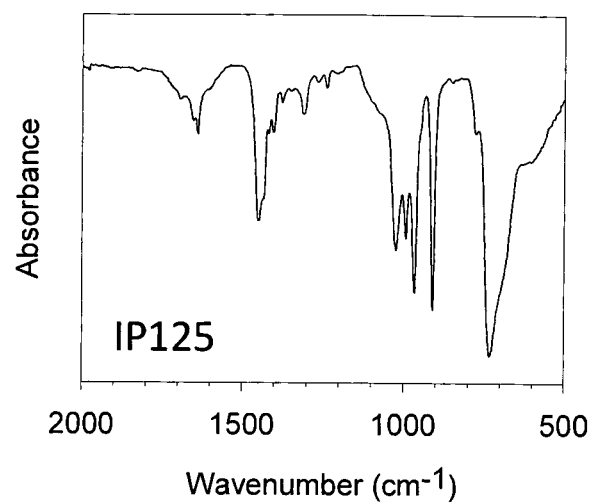
FIG. 27 is the FT-IR spectrum of Example 33.

FIG. 27 shows the FT-IR spectrum of the polybutadiene obtained.

Example 34 (IP125/1)

2 ml of 1,3-butadiene equal to about 1.4 g were condensed, cold (−20° C.), in a 25 ml test tube. Subsequently, 7.9 ml of toluene were added and the temperature of the solution thus obtained was brought to 25° C. Then, methylaluminoxane (MAO) in toluene solution (6.3 ml; $1\times10^{-2}$ moles, equal to about 0.58 g) was added, and, subsequently, the $FeCl_3$(L6) complex [sample MG269] (1.83 ml of toluene solution at concentration of 2 mg/ml; $1\times10^{-5}$ moles, equal to about 3.65 mg) obtained as described in Example 17. Everything was kept under magnetic stirring, at 25° C., for 5760 minutes. The polymerization was then stopped by adding 2 ml of methanol containing some drops of hydrochloric acid. The polymer obtained was then coagulated by adding 40 ml of a methanol solution containing 4% of Irganox® 1076 antioxidant (Ciba) obtaining 0.280 g of polybutadiene having a mixed structure: further characteristics of the process and of the polybutadiene obtained are reported in Table 1.

Figure 28:
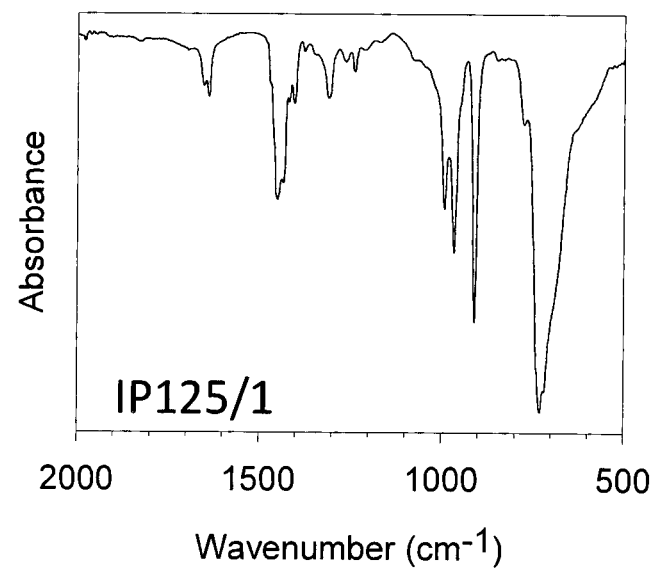
FIG. 28 is the FT-IR spectrum of Example 34.

FIG. 28 shows the FT-IR spectrum of the polybutadiene obtained.

Example 35 (G1534/1)

8.1 ml of toluene and, subsequently, 2 ml of isoprene equal to about 1.36 g were placed into a 25 ml test tube; the temperature of the solution thus obtained was brought to 25° C. Then, methylaluminoxane (MAO) in toluene solution (6.3 ml; $1\times10^{-2}$ moles, equal to about 0.58 g) was added, and, subsequently, the $FeCl_3$(L1) complex [sample MG261] (1.62 ml of toluene solution at concentration of 2 mg/ml; $1\times10^{-5}$ moles, equal to about 3.2 mg) obtained as described in Example 7. Everything was kept under magnetic stirring, at 25° C., for 600 minutes. The polymerization was then stopped by adding 2 ml of methanol containing some drops of hydrochloric acid. The polymer obtained was then coagulated by adding 40 ml of a methanol solution containing 4% of Irganox® 1076 antioxidant (Ciba) obtaining 0.96 g of polyisoprene having a mixed structure: further characteristics of the process and of the polyisoprene obtained are reported in Table 2.

Figure 29:
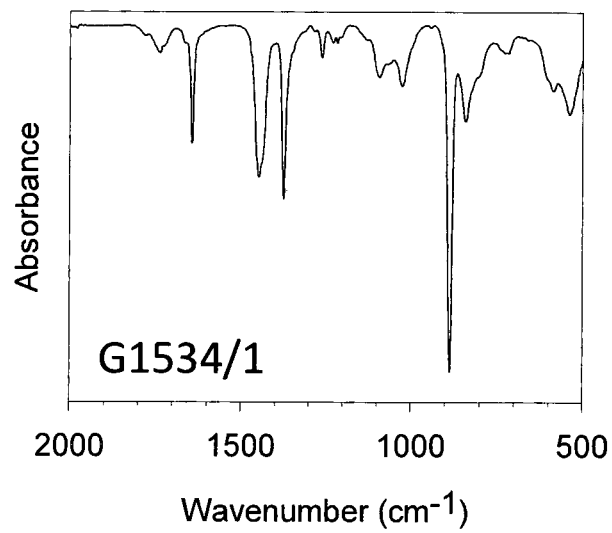
FIG. 29 is the FT-IR spectrum of Example 35.

FIG. 29 shows the FT-IR spectrum of the polyisoprene obtained.

Example 36 (G1535/2)

13.9 ml of toluene and, subsequently, 2 ml of isoprene equal to about 1.36 g were placed into a 25 ml test tube; the temperature of the solution thus obtained was brought to 25° C. Then, methylaluminoxane (MAO) in toluene solution (0.63 ml; $1\times10^{-3}$ moles, equal to about 0.058 g) was added, and, subsequently, the $FeCl_2$(L1) complex [sample MG265] (1.45 ml of toluene solution at concentration of 2 mg/ml; $1\times10^{-5}$ moles, equal to about 2.9 mg) obtained as described in Example 8. Everything was kept under magnetic stirring, at 25° C., for 600 minutes. The polymerization was then stopped by adding 2 ml of methanol containing some drops of hydrochloric acid. The polymer obtained was then coagulated by adding 40 ml of a methanol solution containing 4% of Irganox® 1076 antioxidant (Ciba) obtaining 0.796 g of polyisoprene having a mixed structure: further characteristics of the process and of the polyisoprene obtained are reported in Table 2.

Figure 30:
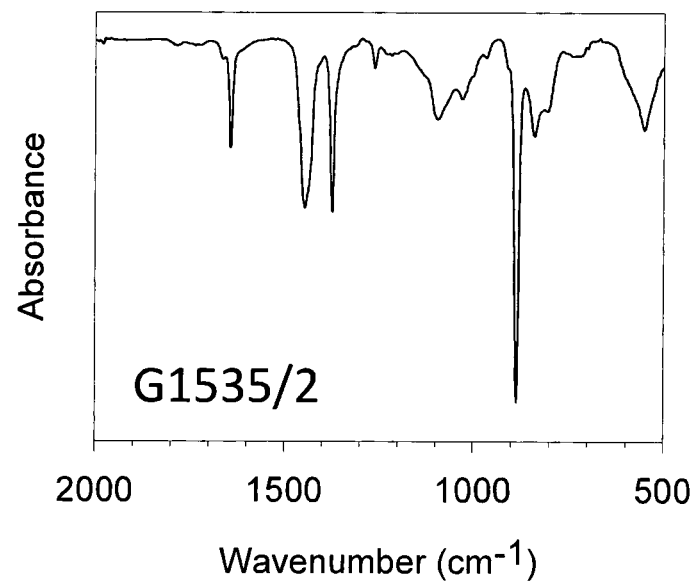
FIG. 30 is the FT-IR spectrum of Example 36.

FIG. 30 shows the FT-IR spectrum of the polyisoprene obtained.

Example 37 (G1537/1)

8 ml of toluene and, subsequently, 2 ml of isoprene equal to about 1.36 g were placed into a 25 ml test tube; the temperature of the solution thus obtained was brought to 25° C. Then, methylaluminoxane (MAO) in toluene solution (6.3 ml; $1 \times 10^{-2}$ moles, equal to about 0.58 g) was added, and, subsequently, the FeCl$_3$(L2) complex [sample MG262] (1.7 ml of toluene solution at concentration of 2 mg/ml; $1 \times 10^{-5}$ moles, equal to about 3.4 mg) obtained as described in Example 9. Everything was kept under magnetic stirring, at 25° C., for 600 minutes. The polymerization was then stopped by adding 2 ml of methanol containing some drops of hydrochloric acid. The polymer obtained was then coagulated by adding 40 ml of a methanol solution containing 4% of Irganox® 1076 antioxidant (Ciba) obtaining 0.541 g of polyisoprene having a mixed structure: further characteristics of the process and of the polyisoprene obtained are reported in Table 2.

Figure 31:
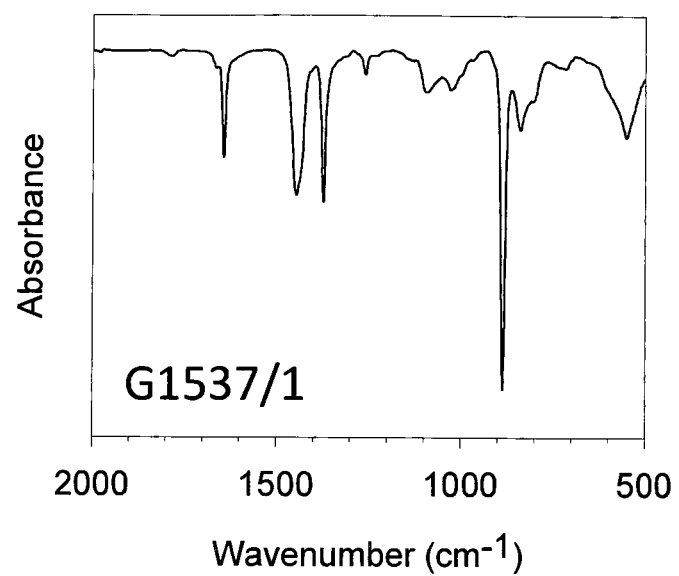
FIG. 31 is the FT-IR spectrum of Example 37.

FIG. 31 shows the FT-IR spectrum of the polyisoprene obtained.

The invention claimed is:

1. Oxo-nitrogenated iron complex having general formula (I):

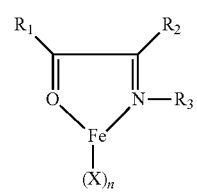

in which:

R$_1$ and R$_2$ are methyl groups;

R$_3$ is selected from the group consisting of phenyl and phenyl groups substituted with one or more methyl, ethyl, iso-propyl, or tert-butyl groups;

X is chlorine; and n is 2 or 3.

2. Catalytic system for the (co)polymerization of conjugated dienes comprising:

(a) at least one oxo-nitrogenated iron complex having general formula (I) according to claim 1;

(b) at least one co-catalyst selected from organic compounds of an element M' different from carbon, said element M' being selected from elements belonging to groups 2, 12, 13, or 14 of the Periodic Table of the Elements.

TABLE 1

Polymerization of 1,3-butadiene with catalytic systems comprising oxo-nitrogenated iron complexes

| Example | Al/Fe (molar ratio) | Time (min) | Conversion (%) | 1,4-cis (%) | 1,4-trans (%) | 1.2 (%) | M$_w$ (g × mol$^{-1}$) | M$_w$/M$_n$ |
|---|---|---|---|---|---|---|---|---|
| 19 | 1000 | 10 | 100 | 38.6 | 0 | 61.4 | 285000 | 2.6 |
| 20 | 100 | 10 | 81.5 | 37.4 | 0 | 62.6 | 341420 | 2.5 |
| 21 | 10 | 20 | 100 | 39.7 | 0 | 60.3 | 405680 | 2.1 |
| 22 | 100 | 15 | 100 | 42.8 | 0 | 57.2 | 335800 | 2.4 |
| 23 | 1000 | 120 | 70.6 | 48.0 | 0 | 52.0 | 182100 | 2.7 |
| 24 | 100 | 120 | 65.9 | 46.4 | 0 | 53.6 | 253970 | 2.6 |
| 25 | 25 | 420 | 31.0 | 52.9 | 0 | 47.1 | 315400 | 2.2 |
| 26 | 25 | 600 | 49.3 | 54.5 | 0 | 45.5 | 298700 | 2.0 |
| 27 | 1000 | 180 | 49.6 | 36.2 | 0 | 63.8 | 201400 | 1.9 |
| 28 | 1000 | 180 | 52.6 | 32.0 | 0 | 68.0 | 197700 | 2.1 |
| 29 | 1000 | 1380 | 26.3 | 79.0 | 5.8 | 15.2 | 97700 | 2.2 |
| 30 | 1000 | 2880 | 46.5 | 76.3 | 5.9 | 17.8 | 94300 | 2.1 |
| 31 | 1000 | 1680 | 12.8 | 79.6 | 3.0 | 17.4 | 91400 | 2.2 |
| 32 | 1000 | 1680 | 17.7 | 78.9 | 4.2 | 16.9 | 87700 | 1.9 |
| 33 | 1000 | 5760 | 10.9 | 78.7 | 8.2 | 13.1 | 79400 | 2.3 |
| 34 | 1000 | 5760 | 20.0 | 80.9 | 6.5 | 12.6 | 73300 | 2.1 |

TABLE 2

Polymerization of isoprene with catalytic systems comprising oxo-nitrogenated iron complexes

| Example | Al/Fe (molar ratio) | Time (min) | Conversion (%) | 1,4-cis (%) | 1,4-trans (%) | 3.4 (%) | M$_w$ (g × mol$^{-1}$) | M$_w$/M$_n$ |
|---|---|---|---|---|---|---|---|---|
| 35 | 1000 | 600 | 70.3 | 40.7 | 0 | 59.3 | 112000 | 2.0 |
| 36 | 100 | 600 | 58.5 | 33.7 | 0 | 66.3 | 99500 | 2.1 |
| 37 | 1000 | 600 | 39.8 | 23.1 | 0 | 76.9 | 87400 | 1.9 |

3. Catalytic system for the (co)polymerization of conjugated dienes according to claim 2, in which said at least one co-catalyst (b) is selected from ($b_1$) an aluminum alkyl having general formula (V):

$$Al(X')_n(R_5)_{3-n} \qquad (V)$$

in which X' represents a halogen atom;

$R_5$, identical or different, represents a hydrogen atom, or is selected from a linear or branched $C_1$-$C_{20}$ alkyl group, a cycloalkyl group, or an aryl group, each of which may be optionally substituted with one or more silicon or germanium atoms; and n is an integer ranging from 0 to 2.

4. Catalytic system for the (co)polymerization of conjugated dienes according to claim 3, in which said aluminum alkyl (b1) having general formula (V) is di-iso-butyl-aluminum hydride (DIBAH), di-ethyl-aluminum chloride (DEAC), mono-ethyl aluminum dichloride (EADC), or ethyl aluminum-sesquichloride (EASC).

5. Catalytic system for the (co)polymerization of conjugated dienes according to claim 2, in which said at least one co-catalyst (b) is selected from an organo-oxygenated compound ($b_2$) of an element M' different from carbon belonging to groups 13 or 14 of the Periodic Table of the Elements.

6. Catalytic system for the (co)polymerization of conjugated dienes according to claim 5, in which said organo-oxygenated compound (b2) is selected from an aluminoxane having general formula (VI):

$$(R_6)_2-Al-O-[-Al(R_7)-O-]_p-Al-(R_8)_2 \qquad (VI)$$

in which $R_6$, $R_7$ and $R_8$, identical or different, represent a hydrogen atom, a halogen atom, or are independently selected from a linear or branched $C_1$-$C_{20}$ alkyl group, a cycloalkyl group, or an aryl group, each of which may be optionally substituted with one or more silicon or germanium atoms; and p is an integer ranging from 0 to 1000.

7. Catalytic system for the (co)polymerization of conjugated dienes according to claim 6, in which said organo-oxygenated compound (b2) is methylaluminoxane (MAO).

8. Catalytic system for the (co)polymerization of conjugated dienes according to claim 2, in which said at least one co-catalyst (b) is selected from an organometallic compound or a mixture of organometallic compounds (b3) of an element M' different from carbon that reacts with the oxo-nitrogenated iron complex having general formula (I) by abstracting from the oxo-nitrogenated iron complex an σ-linked substituent.

9. Catalytic system for the (co)polymerization of conjugated dienes according to claim 8, in which said organometallic compound or mixture of organometallic compounds ($b_3$) is selected from organic compounds of the following general formulae:

$$[(R_C)_wH_{4-w}]\cdot[B(R_D)_4]^-; \; B(R_D)_3; \; Al(R_D)_3;$$
$$B(R_D)_3Pir; \; [Ph_3C]^+\cdot[B(R_D)_4]^-;$$

$$[(R_C)_3PirH]^+\cdot[B(R_D)_4]^-;$$

$$[Li]^+\cdot[B(R_D)_4]^-; \; [Li]^+\cdot[Al(R_D)_4]^-$$

in which w is an integer ranging from 0 to 3, each $R_C$ group independently represents an alkyl group or an aryl group having from 1 to 10 carbon atoms, each $R_D$ group independently represents an aryl group, totally or partially fluorinated, having from 6 to 20 carbon atoms, and Pir is an optionally substituted pyrrole radical.

10. Catalytic system for the (co)polymerization of conjugated dienes according to claim 2, in which said at least one co-catalyst (b) is selected from an organometallic compound or mixture of organometallic compounds (b3) of an element M' different from carbon that reacts with the oxo-nitrogenated iron complex having the general formula (I),
wherein an σ-linked substituent is abstracted by the least one co-catalyst to form:
at least one neutral compound, and
an ionic compound comprising a cation containing the metal (Fe) coordinated by a ligand and a non-coordinating organic anion containing the element M', whose negative charge is delocalized on a multicentric structure.

11. Process for the polymerization of 1,3-butadiene or isoprene, the process comprising polymerizing 1,3-butadiene or isoprene in the presence of the catalytic system according claim 2.

* * * * *